(12) United States Patent
Imura

(10) Patent No.: US 8,345,230 B2
(45) Date of Patent: Jan. 1, 2013

(54) ILLUMINATION APPARATUS AND REFLECTIVE CHARACTERISTICS MEASURING APPARATUS EMPLOYING THE SAME

(75) Inventor: Kenji Imura, Toyohashi (JP)

(73) Assignee: Konica Minolta Sensing, Inc., Osaka (JP)

( * ) Notice: Subject to any disclaimer, the term of this patent is extended or adjusted under 35 U.S.C. 154(b) by 247 days.

(21) Appl. No.: 12/768,206

(22) Filed: Apr. 27, 2010

(65) Prior Publication Data

US 2010/0277728 A1    Nov. 4, 2010

(30) Foreign Application Priority Data

May 1, 2009    (JP) .................................. 2009-111971
Feb. 17, 2010    (JP) .................................. 2010-032757

(51) Int. Cl.
*G01N 21/00*    (2006.01)
(52) U.S. Cl. ...................... 356/237.1; 356/326; 362/346; 362/297; 362/296.09
(58) Field of Classification Search .... 356/237.1–240.1, 356/445–448, 300, 326; 362/600, 609, 611, 362/627, 346, 296.01, 297, 296.09
See application file for complete search history.

(56) References Cited

U.S. PATENT DOCUMENTS

| | | | | |
|---|---|---|---|---|
| 4,943,713 A * | 7/1990 | Yoshida | ..................... | 250/223 B |
| 6,853,446 B1 * | 2/2005 | Almogy et al. | ............. | 356/237.1 |
| 7,006,690 B1 * | 2/2006 | Imura | ........................... | 382/167 |
| 7,365,843 B2 | 4/2008 | Frick et al. | | |
| 7,433,041 B2 | 10/2008 | Frick | | |
| 2009/0066944 A1 * | 3/2009 | Gauffre et al. | ............. | 356/240.1 |

FOREIGN PATENT DOCUMENTS

JP    2008-298579    12/2008

* cited by examiner

*Primary Examiner* — Hoa Pham
(74) *Attorney, Agent, or Firm* — Brinks Hofer Gilson & Lione

(57) ABSTRACT

An illumination apparatus to illuminate a sample surface with excellent illumination efficiency and a reflective characteristics measuring apparatus using the illumination apparatus. The illumination apparatus includes a plane light source positioned on a normal at a center of the sample surface and a mirror having an internal reflective surface positioned between the plane light source and the sample surface. The internal reflective surface has a circular or polygonal shape in a section perpendicular to the normal and the circular or polygonal shape substantially corresponds to an imaginary circle centered on the normal and having a radius equal to half a distance between the plane light source and the sample surface. In place of the mirror, a plurality of reflective faces may be positioned.

31 Claims, 15 Drawing Sheets ured area equals to D1/sin (a), and the density of the light
ILLUMINATION APPARATUS AND REFLECTIVE CHARACTERISTICS MEASURING APPARATUS EMPLOYING THE SAME This application is based on Japanese Patent Application No. 2009-111971 filed on May 1, 2009 in Japanese Patent Office and Japanese Patent Application No. 2010-032757 filed on Feb. 17, 2010 in Japanese Patent Office, the entire contents of which are hereby incorporated by reference.

TECHNICAL FIELD

The present invention relates to an illumination apparatus and a reflection characteristics measuring apparatus employing the same. The reflection characteristic measuring apparatus is an apparatus for measuring reflection characteristic of a color sample. In particular, this reflection characteristics measuring apparatus may be built in a color printer, for example, to scan an array of a plurality of color samples and to perform continuous measurement of reflection characteristics of the color samples, based on which printed colors are calibrated.

BACKGROUND

In a calibration of printed colors in an inkjet printer, for example, a scanner is used to measure an array of a great number of color samples (several hundred color samples) having different color tones and densities (color patch) printed on a sheet according to prescribed input information. Then the spectral reflection characteristics of the visible spectrum (400-700 nm) are measured and calibration is made to eliminate a difference between these measured reflection characteristics and the ideal reference values. To measure the aforementioned spectral reflection characteristics, an illumination receiving system of so-called 45-degrees: 0-degree geometry is used, wherein a sample surface is illuminated at an angle of incidence of 45 degrees with respect to the normal, and the light reflected from the sample surface is received at an angle of reflection of 0 degree relative to the normal. In case of a reflection characteristics measuring apparatus designed for spot measurement, it takes too much time to measure such an array composed of a great number of color samples. To solve this problem, about 20 through 40 color samples arranged in a one-dimensional array are normally measured by manual or automated scanning. Such a reflection characteristics measurement is disclosed, for example, in the Japanese Unexamined Patent Application Publication No. 2008-298579 by the inventor of the present invention.

In such measurement, however, illuminance on a sample surface by the illumination light changes according to a fluctuation in a distance between a measuring instrument and the sample surface resulting from scanning operation. Such change in illuminance results in measurement errors. To minimize the change in illuminance caused by the fluctuation in the distance, an illumination system characterized by reduced change in illuminance caused by the fluctuation in the distance is disclosed and proposed in U.S. Pat. Nos. 7,365,843 and 7,433,041. Such conventional art uses a light source known by the name of cosine emitter or Lambertian emitter. To be more specific, as shown in FIG. 14, the light source S has a spatial distribution of Lambertian characteristics (cosine characteristics), that is, the light source S is a diffusing plane light source. This light source S is arranged in such a way that the center axis X of the spatial distribution will be parallel with the normal N of the sample surface, namely, the light source S and the sample surface will be arranged in parallel with each other, and the distance D1 between the normal N and the center axis X will be equal to the distance D2 between the light source S and the surface including the sample surface. This arrangement ensures that the sample surface is illuminated by the component of light flux from the light source S at an angle of incidence of "a"=45 degrees with respect to the normal N of the sample surface, whereby the aforementioned 45-degrees: 0-degree geometry is implemented.

The following describes the change in illuminance on the sample surface when the distance between the light source S and the surface including the sample surface has changed from D2 to D2+d, the distance L between the light source S and the center O of the measured area on the sample surface has changed to L', and the angle a has changed to a'. The distance L between the light source S and the center O of the measured area equals to D1/sin (a), and the density of the light flux is inversely proportional to the square of the distance L. Thus the density of the light flux is proportional to $\sin^2$ (a). In the meantime, the density of the light flux emitted at an outgoing angle of "a" from the light source S of Lambertian characteristics is proportional to cos (a), and the density of the light flux entering the sample surface at an angle of incidence of "a" is also proportional to cos (a). Thus, the density of the light flux entering the center "O" from the light source S of Lamberitan characteristics is proportional to $\sin^2$ (a)·$\cos^2$ (a), and hence is proportional to $\sin^2$ (2·a). Since the $\sin^2$ (2·a) is maximized at "a"=45 degrees where the differential coefficient is 0, the change ratio in illuminance on the sample surface caused by the change in "a" is minimized when "a" is in the vicinity of 45 degrees. This means that the change ratio in illuminance on the sample surface caused by the change in the distance D2 between the light source S and the surface including the sample surface is minimized when "a" is in the vicinity 45 degrees. FIG. 15 is a chart representing a change in illuminance on the sample surface caused by the fluctuation in the distance between the light source S and the surface including the sample surface in the geometry of FIG. 14. The chart shows a change in illuminance caused by a fluctuation in the distance between the light source S and the surface including the sample surface, when the light source S has the spatial distribution of Lambertian characteristics (◇), and when it has a uniform spatial distribution in the vicinity of 45 degrees independently of angle "a" (□). The "x" axis represents a change ratio in the distance, and the "y" axis indicates a change ratio in illuminance As will be apparent from FIG. 15, in the case of a light source of Lambertian characteristics, a change in illuminance is substantially reduced. For example, when the fluctuation in the distance is 2% (0.16 mm) at D2=D1=8 mm, the illuminance changes 1, and an error of about 1% occurs in the reflection characteristics measurements in case of a light source without Lambertian characteristics. In the case of a light source with Lambertian characteristics, on the other hand, the error is only 0.04%.

As described above, the technique disclosed in U.S. Pat. Nos. 7,365,843 and 7,433,041 substantially reduces a change in illuminance caused by the fluctuation in a distance between the light source S and the surface including the sample surface, namely, a distance between the illumination apparatus and the sample surface. However, the illumination efficiency is extremely poor, because the sample is illuminated by only the component in the vicinity of one direction of 45 degrees relative to the center axis of the spatial distribution of Lambertian characteristics (cosine characteristics) emitted into the hemisphere by the light source S such as an LED.

SUMMARY

The present invention has been made in view of the technical problems described above, and one of the objects of the present invention to provide an illumination apparatus with excellent illumination efficiency and a reflection characteristics measuring apparatus using the illumination apparatus. Another aspect of the present invention to provide an illumination apparatus with a minimized change in illuminance on a sample surface caused by the fluctuation in the distance between a light source and the sample surface, and a reflection characteristics measuring apparatus using the illumination apparatus.

In view of the foregoing, one embodiment according to one aspect of the present invention is an illumination apparatus for illuminating a sample surface to be measured, the illumination apparatus comprising:

a plane light source positioned on a normal passing through a center of a measured area of the sample surface; and a mirror having an internal reflective surface being positioned between said plane light source and said measured area of the sample surface for reflecting light from the plane light source to the measured area, said internal reflective surface having a circular or polygonal shape in a plane perpendicular to said normal, said circular or polygonal shape substantially corresponding to an imaginary circle which is centered on said normal and has a radius equal to half a distance between said plain light source and said measured area of the sample surface.

Another embodiment according to another aspect of the present invention is an illumination apparatus for illuminating a sample surface to be measured, the illumination apparatus comprising:

a plane light source positioned on a normal passing through a center of a measured area of the sample surface; and a plurality of reflective faces being positioned between said plane light source and said measured area of the sample surface and in parallel to said normal for reflecting light from the plane light source to the measured area, said reflective surfaces being positioned at a distance from said normal equal to half a distance between the plane light source and the measured area.

Another embodiment according to another aspect of the present invention is a reflection characteristics measuring apparatus comprising:

a plane light source positioned on a normal passing through a center of a measured area of the sample surface;

a mirror having an internal reflective surface being positioned between said plane light source and said measured area of the sample surface for reflecting light from the plane light source to the measured area, said internal reflective surface having a circular or polygonal shape in a section perpendicular to said normal, said circular or polygonal shape substantially corresponding to an imaginary circle which is centered on said normal and has a diameter equal to a distance between said plane light source and said measured area of the sample surface; and a measuring section, which is adapted to measure reflective characteristic of said measured area of the sample surface based on a light reflected by the measured area of the sample surface.

Another embodiment according to another aspect of the present invention is a reflection characteristics measuring apparatus comprising:

a plane light source positioned on a normal passing through a center of a measured area of the sample surface;

a plurality of reflective faces being positioned between said plain light source and said measured area of the sample surface and in parallel to said normal for reflecting light from the plain light source to the measured area, said reflective surfaces being positioned at a distance from said normal half as long as a distance between the plain light source and the measure area; and a measuring section, which is adapted to measure reflective characteristic of said measured area of the sample surface based on a light reflected by the measured area of the sample surface.

Various aspects and applications of the present invention will become apparent to the skilled artisan upon consideration of the brief description of the figures and the detailed description of the invention which follows.

DETAILED DESCRIPTION OF THE PREFERRED EMBODIMENT

Referring to FIGS. 1 through 15, the following describes the details of the embodiments of the present invention, without the present invention being restricted thereto.

(Embodiment 1)

Figure 1:
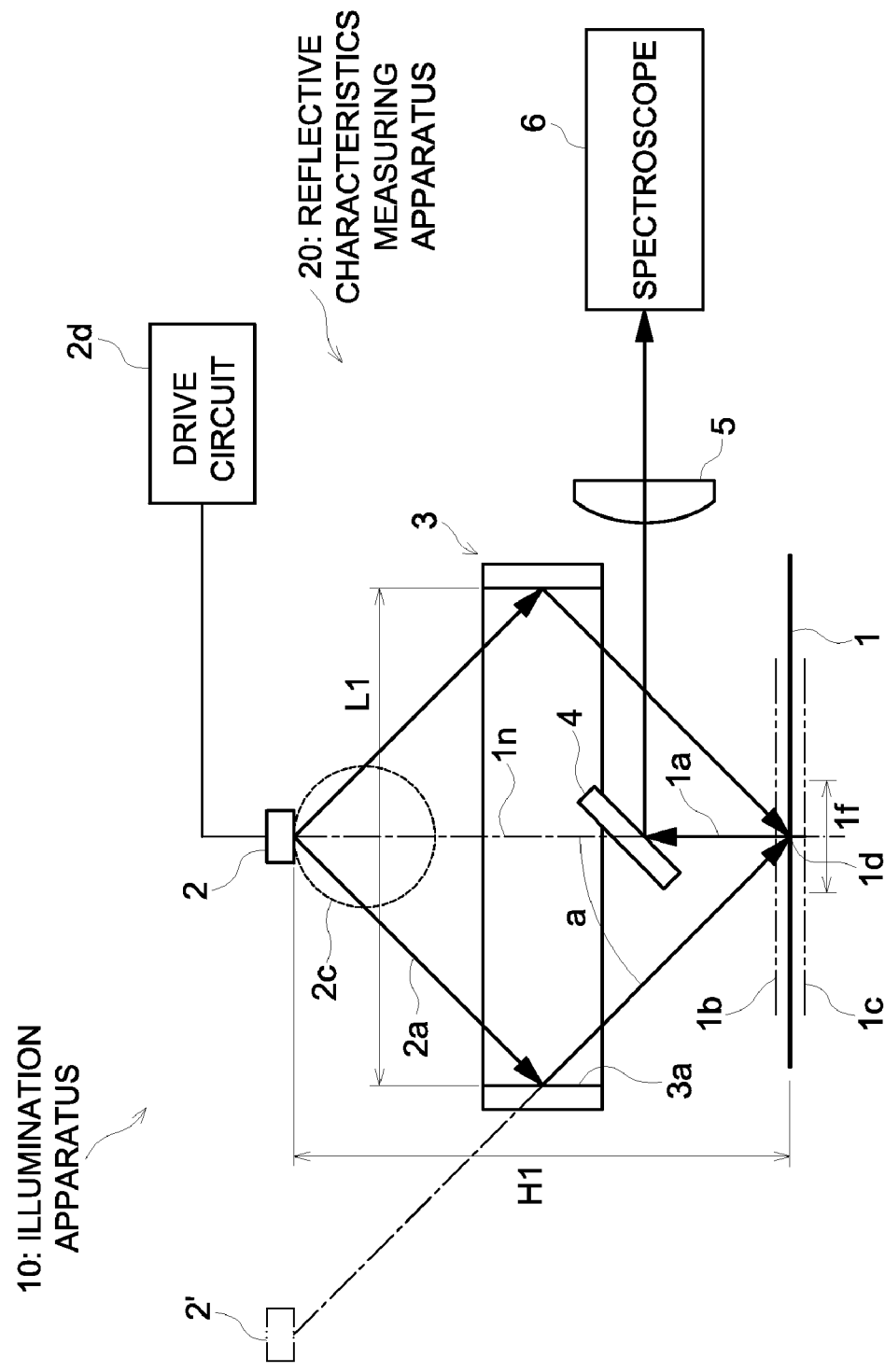
FIG. 1 is a diagram representing the structure of the optical system of the reflection characteristics measuring apparatus employing an illumination apparatus, as a first embodiment of the present invention.

FIG. 1 is a diagram representing the structure of an optical system of a reflection characteristics measuring apparatus 20 employing with an illumination apparatus 10, as a first embodiment of the present invention. The reflection characteristics measuring apparatus 20 is built, for example, in an inkjet color printer, and is used to scan a color patch printed on a sheet as a measured area on the sample surface 1 according to the predetermined input information and to measure the spectral reflection characteristics. After that, the color printer is subjected to calibration to eliminate the difference between measured reflection characteristics and ideal reference values. This color printer is used, for example, for a proof printing prior to production printing and to perform color adjustment.

To measure the spectral reflection characteristics, this optical system uses the illumination apparatus 10 to illuminate the sample surface 1 at an angle of "a"=45 degrees with respect to the normal $1n$ passing through the center $1d$ of the measured area $1f$ on the sample surface 1, and the light reflected from the sample surface is received at an angle of reflection of 0 degree with respect to the normal $1n$, whereby the so-called 45-degree: 0-degree geometry is configured. To implement this configuration, the illumination apparatus 10 includes a first plane light source 2 positioned on the normal $1n$; a drive circuit $2d$ for driving the first plane light source 2 to emit light; and a cylindrical surface mirror having an internal reflective surface. The reflective surface of the cylindrical surface mirror is positioned between the sample surface 1 and the first plane light source 2, and the light flux emitted by the first plane light source 2 is reflected by the internal reflective surface of the cylindrical mirror, whereby the sample surface 1 is illuminated. Further, the section of the reflective surface becomes circular wherein the normal $1n$ coincides to a center axis, and the radius of this circle is equal to half the distance between the sample surface and the first plane light source.

The first plane light source 2 is a white LED, for example, and has a spatial distribution $2c$ of Lambertian characteristics (cosine characteristics), as shown in FIG. 1. Thus, the sample surface 1 is illuminated from all directions by the light flux which is emitted from the plane light source 2 at an angle of about 45 degrees with respect to the normal $1n$ and is reflected by the internal reflective surface of the cylindrical surface mirror 3. The component $1a$ reflected by the sample surface in the direction of normal $1n$ changes its optical path in the direction parallel to the sample surface after having being reflected by the reflecting mirror 4 arranged on the normal $1n$. Then, the component $1a$ enters a spectroscope 6 after being converged by an objective lens 5, wherein the spectral distribution is measured. The illumination apparatus 10, the reflecting mirror 4, objective lens 5 and spectroscope 6 constitutes the reflection characteristics measuring apparatus 20.

In the reflection characteristics measuring apparatus 20 having the aforementioned structure, taking the reflective surface $3a$ on the upper left side (in this paper) of the cylindrical surface mirror 3, for example. The sample surface 1 is illuminated by the light source image 2' (i.e. the image of the first plane light source 2) having the Lambertian characteristics located at the position symmetrical with the first plane light source 2 with respect to this reflective surface $3a$. Applying this to the entire reflective surface of the mirror 3, the sample surface 1 is illuminated by numberless light source images of Lambertian characteristics on the circumference including the light source image 2', wherein a center of the circumference is on the normal $1n$. Thus, assume that the incident angle of the illumination light is "a". Similarly to the illumination optical system disclosed in U.S. Pat. Nos. 7,365,843 and 7,433,041 using the conventional light source of the Lambertian characteristics shown in FIGS. 14 and 15, the illuminance on the sample surface 1 changes in proportion to sin (2a) according to the fluctuation of the incident angle "a" caused by the fluctuation in distance between the first plane light source 2 and the sample surface 1 (the fluctuation in the height of the sample surface 1 is shown by the virtual lines $1b$ and $1c$ in FIG. 1). Thus, the ratio of changes in illuminance caused by the fluctuation in the distance becomes close to 0 at "a"=about 45 degrees. In the meantime, the sample surface 1 is illuminated from all azimuthal directions by all azimuthal components of the light flux emitted at about 45 degrees with respect to the center axis (the normal $1n$ of the sample surface 1) of the spatial distribution of the first plane light source 2 having Lambertian characteristics. Thus, the efficiency of light flux usage is much higher than that of the illumination optical system disclosed in U.S. Pat. No. 7,365,843 wherein the sample surface is illuminated only by the components of light flux emitted in the vicinity of one direction. Further, as compared to the 45-degree: 0-degree geometry shown in U.S. Patent No. 7,433,041 wherein illumination is given by the components of the light flux emitted in the vicinity of one direction, the method of illumination from all azimuthal directions has the advantage of the 45-degree a: 0-degree geometry which ensures greater stability against the inclination or anisotropy of the sample surface 1.

In U.S. Pat. No. 7,433,041, many light sources are distributed on the circumference, instead of the cylindrical surface mirror 3 in the present embodiment. According to this configuration, the amount of light at the sample surface 1 can be increased in response to the number of the arranged light sources. However, out of the components in the vicinity of 45 degrees with respect to the center axis of spatial distribution, only the component in the vicinity of one direction can be used. In this respect, this configuration is similar to that of U.S. Pat. No. 7,365,843 and has a similar disadvantage of very low illumination efficiency. In the present embodiment, only the component in the vicinity of 45 degrees with respect to the center axis of the spatial distribution can be used. In this respect, the present embodiment is the same as U.S. Pat. Nos. 7,365,843 and 7,433,041. Regarding the azimuthal direction, however, while only the component in the vicinity of one direction can be used in U.S. Pat. Nos. 7,365,843 and 7,433, 041, the components from all directions distributed from the light source can be used, and hence the efficiency of the light flux usage can be increased by 10 through 20 times.

As compared to U.S. Pat. No. 7,433,041 that requires a great number of LEDs to be arranged, the present embodiment requires only one white LED, which leads to a substantial reduction of costs and power consumption. Further, as disclosed in U.S. Pat. No. 7,433,041, a white LED is driven at a constant voltage and the forward voltage while the white LED is driven is detected to monitor the intensity of light emission. Compared to the illumination optical system disclosed in U.S. Pat. No. 7,433,041 employing a great number of LEDs, the present embodiment requires detection of the forward voltage of only one LED, which enables simplified structure and lesser costs.

According to the present embodiment, in an apparatus for illuminating the sample surface with respect to which spectral reflection characteristics and others are measured, the plane light source such as LED having the spatial distribution of Lambertian characteristics (cosine characteristics) is adopted as a light source. Further, the light flux emitted from the plane light source is reflected by the cylindrical surface mirror 3 to illuminate the sample surface 1. This arrangement ensures that the sample surface is illuminated from the direction of incidence of 45 degrees with respect to the normal, and the light reflected from the sample surface is received at an angle of reflection of 0 degree with respect to the normal, whereby the so-called 45-degree: 0-degree geometry is implemented. Further, the sample surface is equivalently illuminated by numberless light source images of Lambertian characteristics on the circumference whose radius is equal to the distance between the sample surface and plane light source, wherein the plane light source is at a center of the circumference.

Thus, the numberless light source images on the circumference work as Lambertian light sources wherein the distance from the surface including the sample surface is equal to the distance from the normal of the sample surface. Similarly to the case of the illumination optical system disclosed in U.S. Pat. Nos. 7,365,843 and 7,433,041, this arrangement in the present embodiment reduces the fluctuation in illumination on the sample surface caused by the fluctuation in distance between the light source and the sample surface. Further, similarly to these conventional techniques, out of the spatial distribution having Lambertian characteristics, only the components in the vicinity of 45 degrees with respect to the center axis is used. In the present embodiment, on the other hand, all the light fluxes emitted in all azimuthal directions from the plane light source can be used. Thus, the efficiency of the light flux usage is much higher than that of the illumination optical system disclosed in U.S. Pat. Nos. 7,365,843 and 7,433,041 wherein only the component in the vicinity of one direction can be used. Further, in contrast to the 45-degree: 0-degree geometry disclosed in U.S. Pat. No. 7,365,843 wherein illumination is given by the component in the vicinity of one direction, illumination is given from all azimuthal directions in the present embodiment. This provides the advantage of the 45-degree a: 0-degree geometry (a: annular) which ensures stability against the inclination or anisotropy of the sample surface.

In the aforementioned embodiment, the entire internal surface of the cylindrical surface mirror member needs not always be a continuous (connected throughout the entire periphery) reflective surface, but may be formed of a plurality of separated reflective faces. Similarly, the cylindrical member supporting the cylindrical surface mirror need not always be a continuous (connected throughout the entire periphery) cylindrical member. The cylindrical member can be separated in conformance to the support member of the component for receiving optical system. The radius of the circle in the section centered on the normal needs not be strictly the same as half the distance between the sample surface and the plane light source, but may be substantially the same.

(Embodiment 2)

Figure 2:
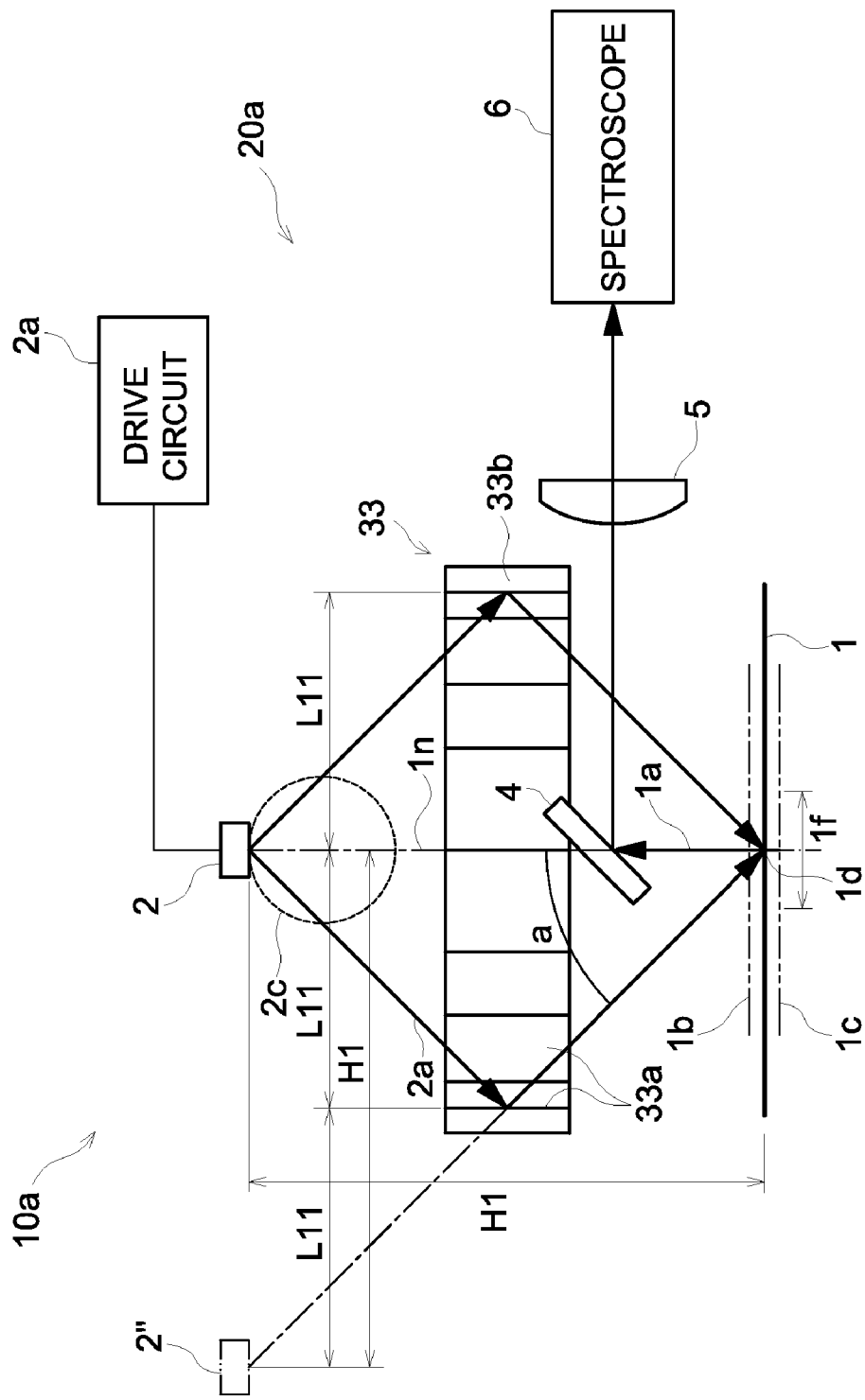
FIG. 2 is a diagram representing the structure of the optical system of the reflection characteristics measuring apparatus equipped with an illumination apparatus, as a second embodiment of the present invention.

FIG. 2 is a diagram representing the structure of the optical system of the reflection characteristic measuring apparatus 20a employing an illumination apparatus 10a, as a second embodiment of the present invention. This reflection characteristic measuring apparatus 20a is similar to the aforementioned reflection characteristic measuring apparatus 20 except that only the illumination apparatus 10a is different from the illumination apparatus 10. Accordingly, the corresponding portions will be assigned with the same reference symbols, and will not be described to avoid duplication. It should be noted that the illumination apparatus 10a of the reflection characteristics measuring apparatus 20a employs a polyhedral mirror 33 having the internal reflective surface wherein the section perpendicular to the normal is polygonal, instead of the cylindrical surface mirror 3 in the illumination apparatus 10.

Figure 3A:
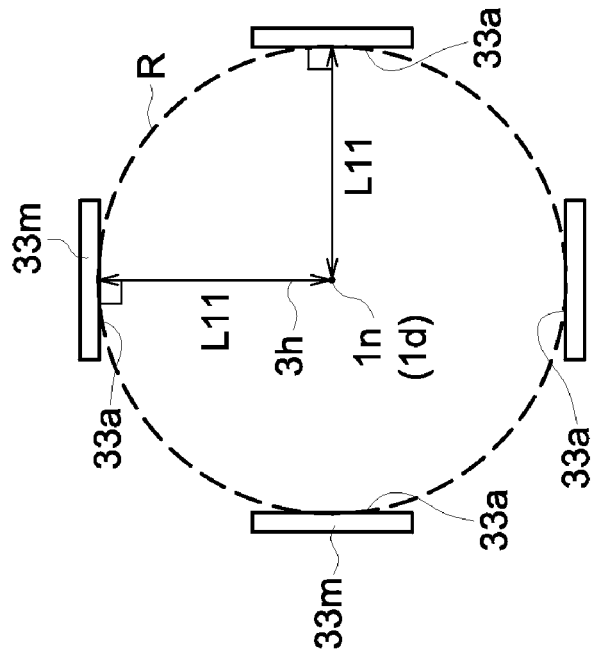
FIGS. 3a, 3b and 3c are the diagrams showing the function of a polyhedral mirror in the reflection characteristics measuring apparatus shown in FIG. 2.

FIG. 3a is a plan view showing an example of the polyhedral mirror 33. This polyhedral mirror 33 includes a plurality of reflective faces 33a (the number of faces is 16 in FIG. 3, but can be other even or odd numbers) formed by attaching plane reflective mirrors on the internal side of the sleeve member 33b, for example. Each of the reflective faces 33a is installed wherein the distance L11 from the normal 1n passing through the center 1d of the measured area on the sample surface 1 is equal to half the distance H1 between the sample surface 1 and the first plane light source 2. To put it another way, each of the reflective faces 33a is arranged so that the section perpendicular to the normal 1n is polygonal, and this polygon circumscribes an imaginary circle whose radius is half the distance H1 between the sample surface 1 and the first plane light source 2.

This arrangement allows the sample surface 1 to be illuminated from the direction of incidence of 45 degrees with respect to the normal 1n and the light reflected from the sample surface is received at an angle of reflection of 0 degree with respect to the normal 1n, whereby the so-called 45-degree: 0-degree geometry is implemented. Further, the sample surface 1 is equivalently illuminated by a great number (16 in FIG. 3) of light source images 2'' having Lambertian characteristics on the circumference, wherein the first plane light source 2 is at a center, and the radius is equal to half the distance H1 between the sample surface 1 and the first plane light source 2.

Thus, a great number of the aforementioned light source images 2'' are Lambertian light sources wherein the distance H1 from the surface including the sample surface 1 is equal to the distance from the normal 1n of the sample surface. Similarly to the case of the illumination optical system described in U.S. Pat. Nos. 7,365,843 and 733,041, this arrangement in the present embodiment reduces the fluctuation in illuminance on the sample surface 1 caused by the fluctuation in the distance between the first plane light source 2 and the sample surface 1. Similarly to these conventional techniques, only the component in the vicinity of 45 degrees with respect to the center axis (normal 1n of the sample surface 10 of the spatial distribution having Lambertian characteristics is used. This arrangement ensures that the majority of the light flux emitted from the first plane light source 2 in all azimuthal directions is converged on the sample surface 1. As compared to the illumination optical system disclosed in U.S. Pat. Nos. 7,365,843 and 733,041 wherein only the component in the vicinity of one direction can reach the sample surface, the components in the vicinity of 16 azimuthal directions can reach the sample surface be utilized in the present embodiment, wherein the efficiency of the light flux usage can be increased by about 10 times. Further, in contrast with the 45-degree: 0-degree geometry disclosed in U.S. Pat. No. 7,365,843, the method of illumination from multiple azimuthal directions provides the advantage of the 45-degree c: 0-degree geometry which ensures greater stability against the inclination or anisotropy of the sample surface 1.

Further, the inverse square law is based on the assumption that there is no refraction between a light source and an illumination surface. In the case of the cylindrical surface mirror 3, the inverse square law does not exactly hold due to the partial refraction (convergence) by the cylindrical surface mirror 3. In the vicinity of 45 degrees with respect to the center axis, the illuminance on the sample surface 1 is inversely proportional to the distance by the power of "n" (n<2). In the case of the polyhedral mirror 33 of the present embodiment, by contrast, there is no refraction, and hence the inverse square law exactly holds, thereby sufficiently reducing the change in illuminance on the sample surface caused by the fluctuation in distance.

Figure 3B:
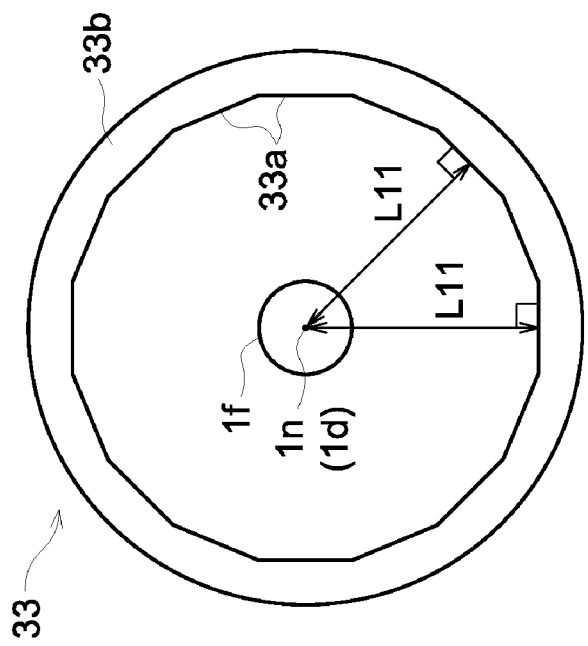
Figure 3C:
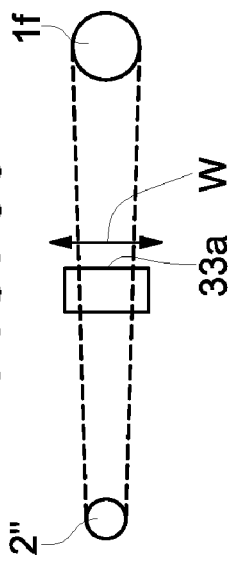

As described above, the change in illuminance is close to 0 at the incident angle "a"=45 degrees. This is based on the premise that the density of light flux is inversely proportional to the square of distance H1. To ensure this premise, all the components of the light flux from the first plane light source 2 emitted in the direction to reach the sample surface 1 should not be hindered. Therefore, the reflective face 33a of the polyhedral mirror 33 is required to have the size large enough to reflect all components to reach the sample surface 1. In this arrangement, the reflective face 33a should be formed to have a sufficient length in the direction of height H1 parallel to the normal 1n, which may be easily implemented due to less spatial constraint in the direction of height H1. At the same time, as shown in FIG. 3c, the reflective face 33 should have the width W perpendicular to the height H1 sufficient to reflect all components of the light flux from the light source image 2" emitted in the directions to reach the measured area 1f of the sample surface 1, which should be more carefully determined. As the number of the surfaces of the polyhedral mirror 33 is greater, a greater number of light source images 2" are provided, whereby the efficiency of the light flux usage is improved. Thus, in the present embodiment, the number of divisions is set at 16, as described above, in such a way that a required width W for the premise with a margin is given to each reflective surface 33a and, at the same time, the efficiency of the light flux usage is maximized.

Further, the entire internal surface of the cylindrical member 33b is not required to be continuous (connected throughout the entire periphery) reflective surface. As shown in FIG. 3b, a plurality of reflective mirrors 33m, each having a plurality of reflective faces 33a, should be arranged at an equally spaced interval in the circumferential direction so as to subscribe the imaginary circle R wherein the radius from the normal 1n is L11. The reflective mirrors 33m should not necessarily be hold in a cylindrical mirror but may be each connected by a desired connecting member such as a frame member without being restricted to the cylindrical member, and should be held so as to minimize the eccentricity with respect to the normal 1n.

According to the present embodiment, in the apparatus for illuminating the sample surface with respect to which spectral reflection characteristics and others are measured, a plane light source such as LED having the spatial distribution of Lambertian characteristics (cosine characteristic) is adopted as a light source. The light flux emitted by the plane light source is reflected by the polyhedral mirror positioned between the sample surface and the plane light source and illuminates the sample surface. This polyhedral mirror includes a plurality of reflective faces formed by attaching reflective mirrors inside the cylindrical member. Not all the faces of the cylindrical member are required to be reflective faces. A plurality of reflective faces are each arranged at the position wherein the distance from the normal at the center of the measured area on the sample surface is equal to half the distance between the sample surface 1 and the plane light source 2. To put it another way, the section of a plurality of reflective surface is polygonal centered at the normal, and this polygon circumscribes an imaginary circle whose radius is half the distance between the sample surface and the first plane light source. This arrangement allows the sample surface to be illuminated at an angle of incidence of 45 degrees with respect to the normal and the light reflected from the sample surface is received at an angle of reflection of 0 degree with respect to the normal, whereby the so-called 45-degree : 0-degree geometry is implemented. Further, the sample surface is equivalently illuminated by a plurality of light source images having Lambertian characteristics on the circumference wherein the plane light source is at a center, and the radius is equal to half the distance between the sample surface and plane light source.

Thus, many light source images are the Lambertian light sources wherein the distance from the surface including the sample surface and the distance from the normal of the sample surface are equal to each other. Similarly to the illumination optical system disclosed in U.S. Pat. Nos. 7,365,843 and 7,433,041, it is possible to reduce the change in illuminance caused by the fluctuation in the distance between the light source and the sample surface. Similarly to these conventional techniques, out of the spatial distribution having Lambertian characteristics, only the components emitted in the vicinity of 45 degrees with respect to the center axis is used. Unlike these conventional techniques, the majority of the light flux emitted in all azimuthal directions from the plane light source can be converged on the sample surface. Thus, the efficiency of the light flux usage is much higher than that of the illumination optical system disclosed in U.S. Pat. Nos. 7,365,843 and 7,433,041 wherein only the component of the light flux emitted in the vicinity of one direction can be used.

Further, the inverse square law holds when no refraction occurs in the light path between the light source and an illumination surface. In the case of the cylindrical surface mirror 3, the inverse square law does not exactly hold due to the partial refraction (convergence) by the cylindrical surface mirror. In the case of the polygon mirror, by contrast, there is no refraction on the reflective face of the polygon mirror, and hence the inverse square law exactly holds thereby reducing the changes in illuminance on the sample surface caused by the fluctuation in the distance. The method according to the present embodiment provides the advantage of the 45-degree c: 0-degree geometry (c: circumferential) which ensures greater stability against the inclination or anisotropy of the sample surface.

According to the aforementioned embodiment, the reflective faces 33a are arranged so that the section perpendicular to the normal is polygonal centered on the normal, and this polygon circumscribes an imaginary circle whose radius is half the distance H1 between the sample surface 1 and the first plane light source 2. This polygon may inscribe the imaginary circle or may be located intermediate between circumscribed and inscribed position.

(Embodiment 3)

Figure 4:
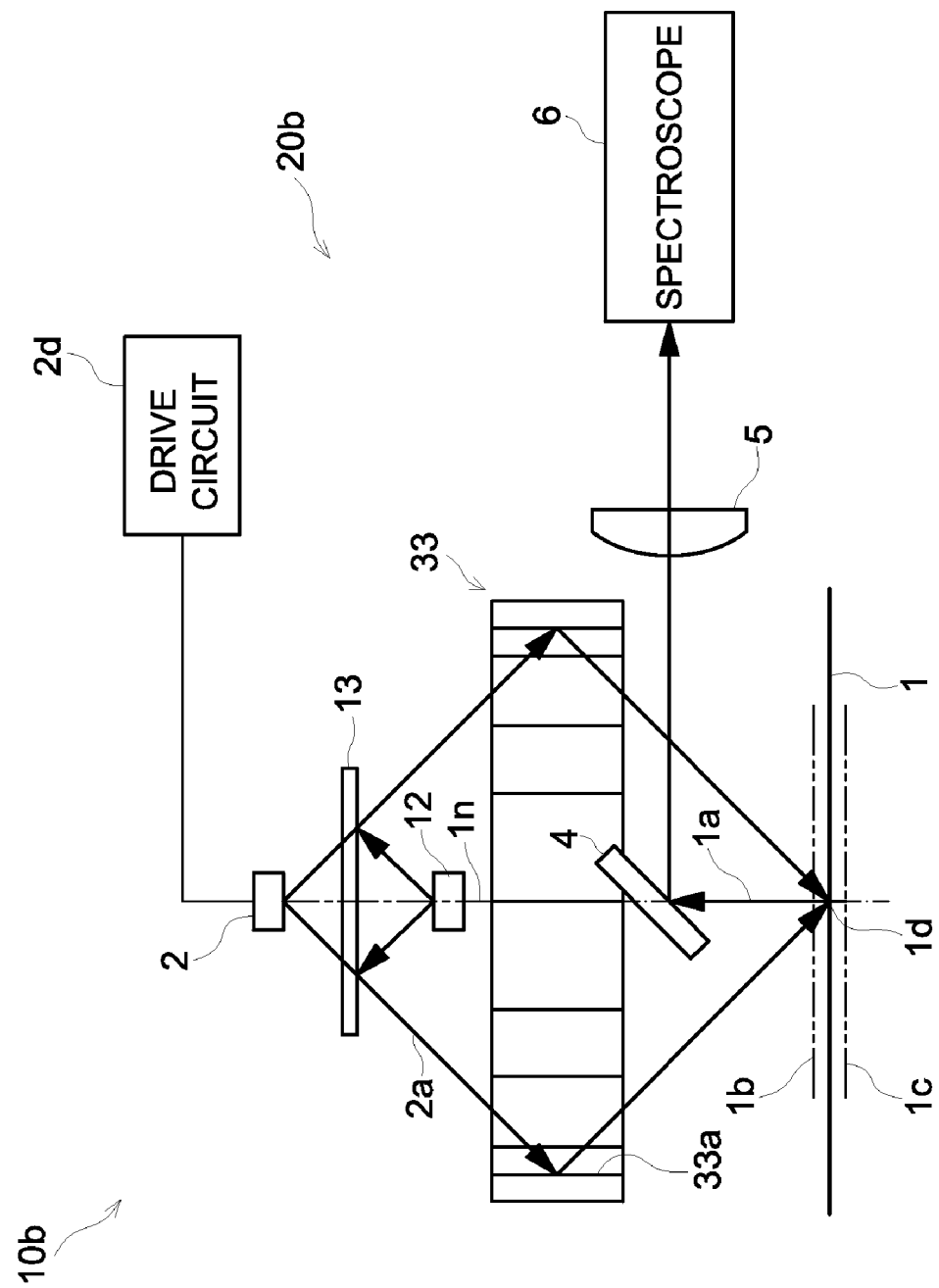
FIG. 4 is a diagram representing the structure of the optical system of the reflection characteristics measuring apparatus equipped with an illumination apparatus, as a third embodiment of the present invention.

FIG. 4 is a diagram representing the optical system of the reflection characteristic measuring apparatus 20b equipped with an illumination apparatus 10b as a third embodiment of the present invention. This reflection characteristic measuring apparatus 20b is similar to the aforementioned reflection characteristic measuring apparatuses 20 and 20a, except that only the illumination apparatus 10b is different from the illumination apparatuses 10 and 10a. Accordingly, the corresponding portions will be assigned with the same reference symbols, and will not be described to avoid duplication. These reflection characteristic measuring apparatuses 20 and 20a are incorporated in the inkjet color printer. Therefore, frequency of maintenance should be minimized and a white LED which has long service life due to having neither burnout nor deterioration of filament is used as the first plane light source 2 to measure a visible spectrum .

Figure 5:
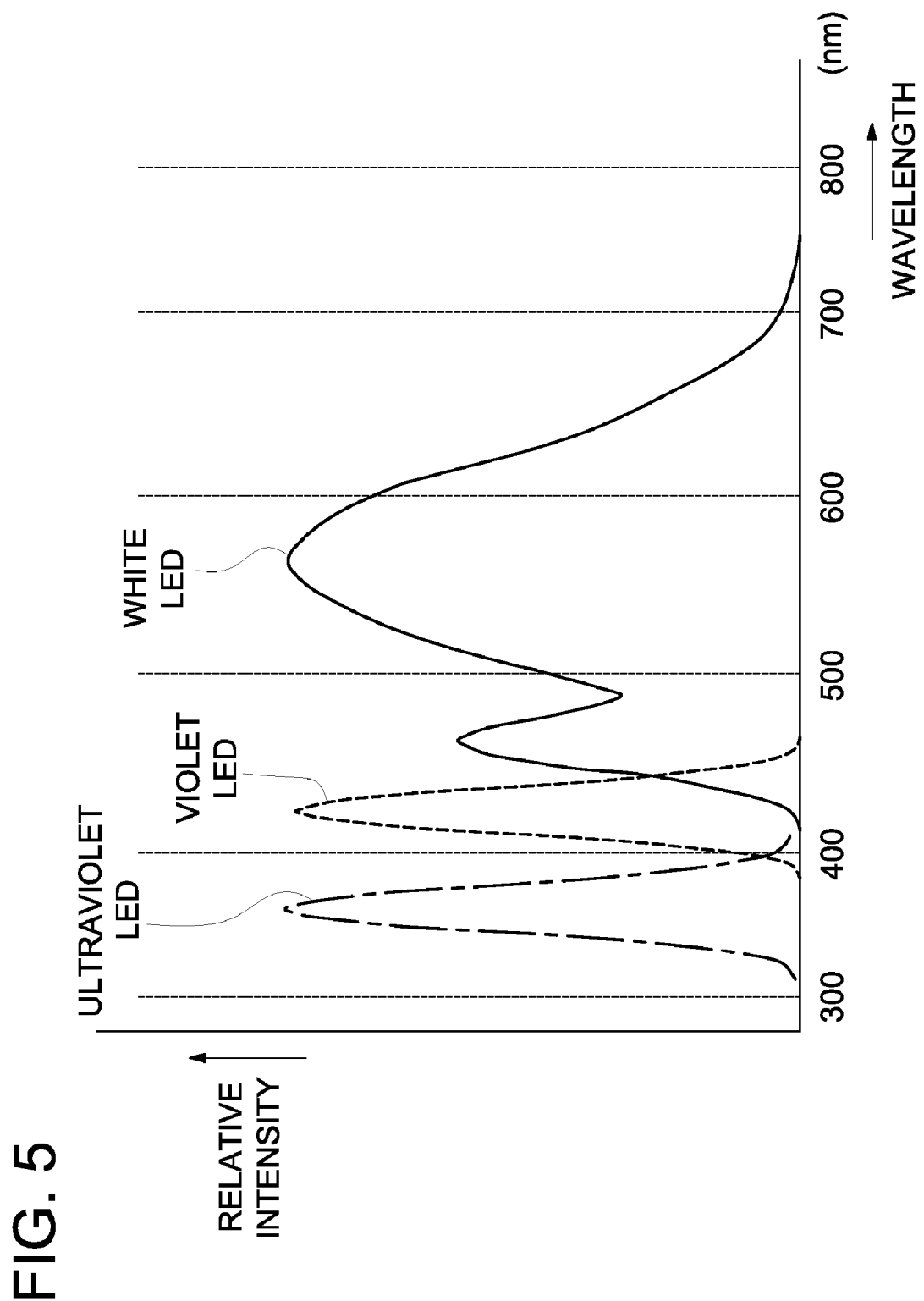
FIG. 5 is a chart showing an example of the spectral intensity distribution of a white LED, violet LED and ultraviolet LED.

As shown in FIG. 5, a spectral intensity distribution of the white LED is low on both ends of the visible spectrum (400-700 nm). Especially, there is almost no intensity below 430 nm. As calibration of printed colors requires the spectral intensity distribution over the entire visible spectrum, the first plane light source 2 formed of a white LED is used as a main light source, and a violet LED covering the short wave range is used as a secondary light source in combination in many cases. Calibration of printed colors on a fluorescent whitened paper requires an illumination having intensity in the ultraviolet region for exciting the fluorescent whitening agent. To meet this requirement, the ultraviolet LED may be used as a secondary light source in combination. Similarly to the case of the white LED used as a main light source, such an additional secondary light source is required to ensure that a change in illuminance caused by fluctuation in the distance is reduced and the efficiency of the light flux usage is increased.

It should be noted that, in this illumination apparatus 10*b*, when further providing a secondary light source for supplementing such spectral intensity distribution, such secondary light source should have the spatial distribution of Lambertian characteristics (cosine characteristic), similarly to the case of the first plane light source 2, and such secondary light source is used as the second plane light source 12. Further, a member for combining the light flux emitted from the first plane light source 2 and the light flux emitted from the second plane light source 12, for example, a dichroic mirror or a semitransparent mirror (hereinafter referred to as "dichroic mirror") 13 is installed between the polyhedral mirror 33 and the first plane light source 2. The second plane light source 12 is placed at a position symmetrical to the first plane light source 2 with respect to the dichroic mirror 13. The dichroic mirror 13 is produced by a multilayer coating for transmitting the longer wavelength light than 440 nm, for example, and reflecting the shorter wavelength light. Thus this dichroic mirror 13 transmits the light flux emitted from the first plane light source 2 of a white LED, while reflecting the light flux emitted from the second plane light source 12 formed of a violet LED, to the polyhedral mirror 33, whereby the sample surface 1 is illuminated.

This arrangement ensures that the light flux 2*a* coming from the first plane light source 2 as a main light source is reflected by the polyhedral mirror 33 after passing through the dichroic mirror 13 as described above, and illuminates the sample surface 1 at an angle of 45 degrees of incidence from multiple directions. This arrangement also ensures that the light flux 12*a* coming from the second plane light source 12 as a secondary light source is reflected by the polyhedral mirror 33 after being reflected by the dichroic mirror 13, and illuminates the sample surface 1 at an angle of 45 degrees of incidence from multiple directions. As such, this arrangement forms substantially the same arrangement of the illumination optical system in FIG. 2. Similarly to the case of the main light source, the secondary light source also increases the efficiency of the light flux usage while reducing a change in illuminance on the sample surface 1 caused by the fluctuation of the distance between the illumination apparatus 10*b* and the sample surface 1. Further, this arrangement provides the advantage of the 45-degree : 0-degree geometry which ensures greater stability against the inclination or anisotropy of the sample surface 1. Further, combining two light fluxes allows the sample surface 1 to be illuminated by the illumination light of the spectral intensity distribution covering the range from 400 through 700 nm.

The present embodiment permits additional installation of a secondary light source having a spectral intensity distribution for supplementing a first plane light source. For example, when a white LED is used as a first plane light source, a violet LED having intensity in the short wavelength range is used as the secondary light source to cover such range wherein the white LED has no intensity, whereby the entire visible spectrum can be covered. Further, an ultraviolet LED used as the secondary light source will make it possible to measure the sample surface including the fluorescent whitening agent wherein the ultraviolet component of the illumination is partly converted to a visible emission.

Further, in the present embodiment, when the first plane light source is installed as the main light source, and the second light source is further installed as the secondary light source for supplementing the spectral intensity distribution of the main light source, a member for combining the light flux emitted from the first plane light source 2 and the light flux emitted from the second plane light source 12, such as a dichroic mirror or a semitransparent mirror is installed between the polyhedral mirror and the first plane light source. At the same time, the second plane light source is placed at a position symmetrical to the first plane light source with respect to the aforementioned mirror. In this arrangement, similarly to the case of the main light source, the secondary light source also increases the efficiency of the light flux usage while reducing a change in illuminance on the sample surface caused by the fluctuation of the distance between the illumination apparatus and the sample surface. Further, this arrangement provides the advantage of the 45-degree c: 0-degree geometry which ensures greater stability against the inclination or anisotropy of the sample surface.

(Embodiment 4)

Figure 6:
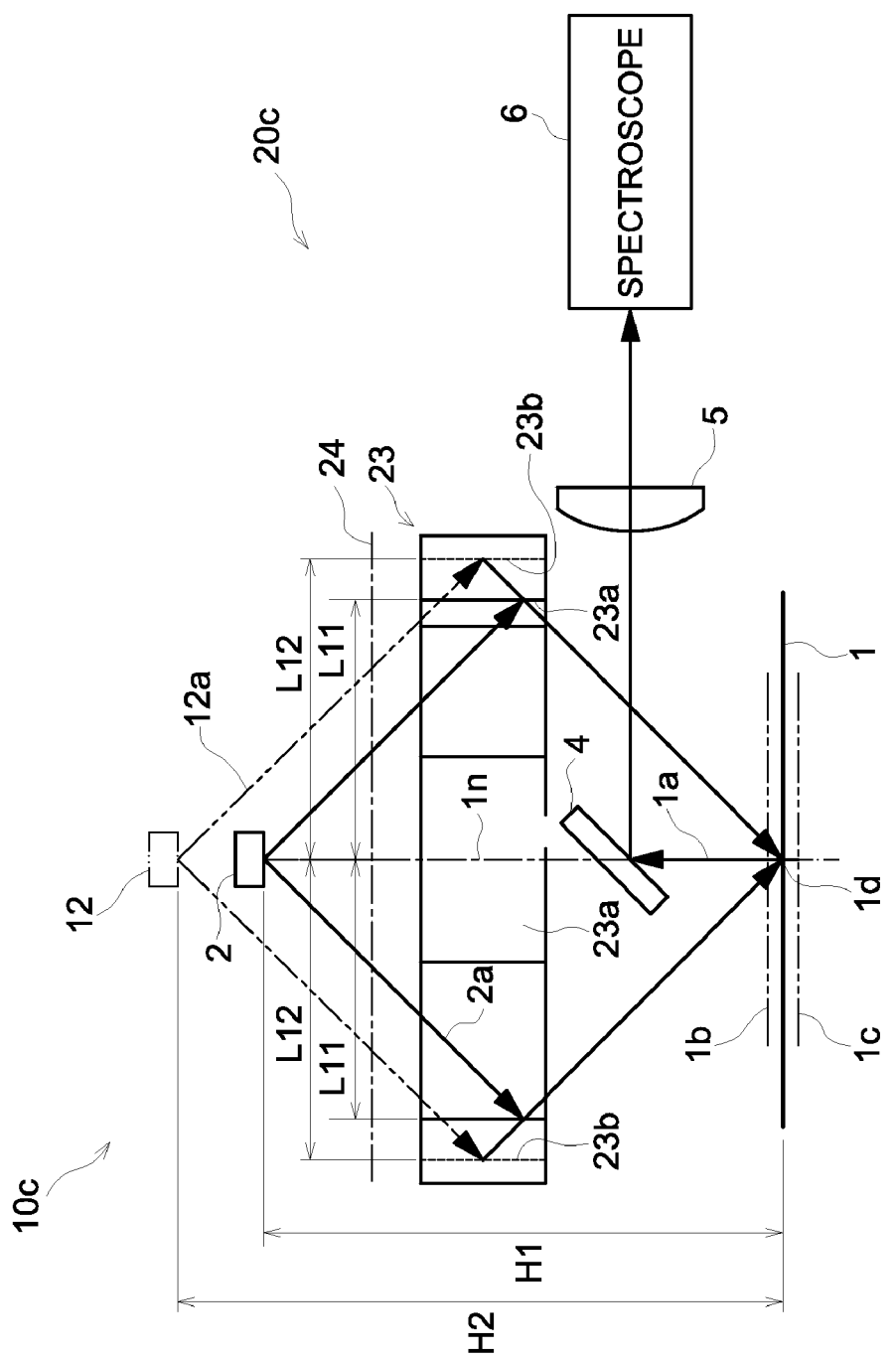
FIG. 6 is a diagram representing the structure of the optical system of the reflection characteristics measuring apparatus equipped with an illumination apparatus, as a fourth embodiment of the present invention.
Figure 7:
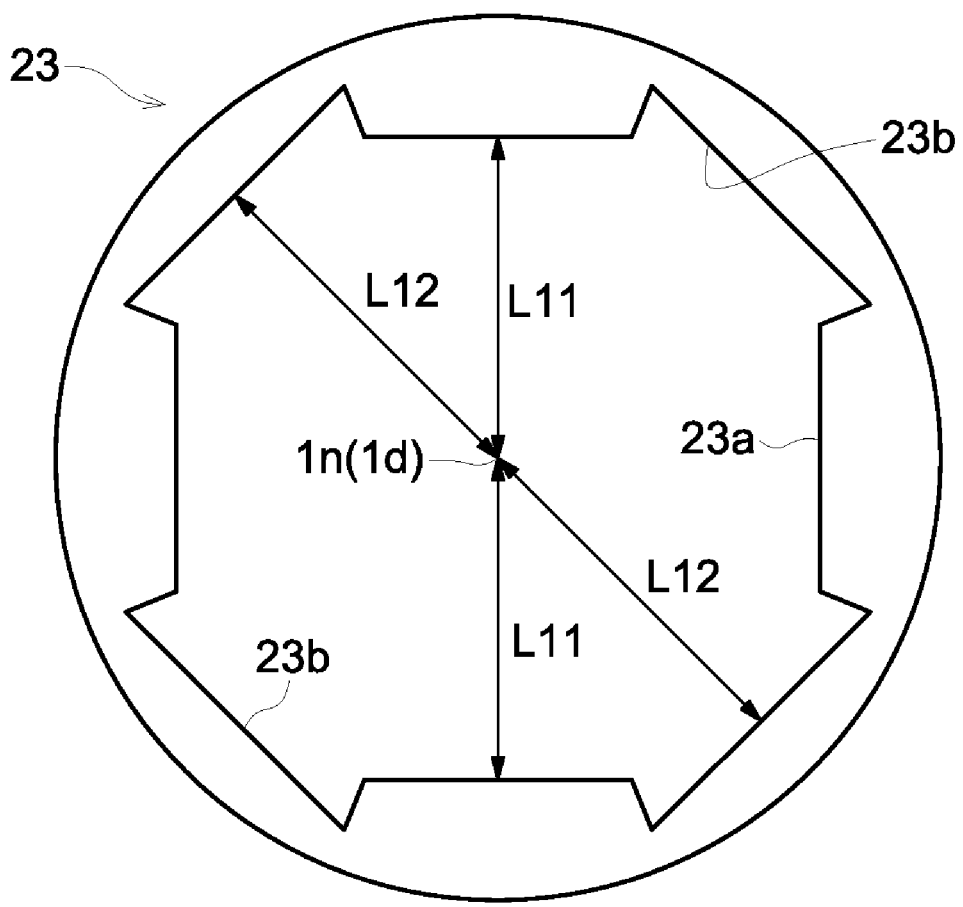
FIG. 7 is a plan view of a polyhedral mirror in the illumination apparatus of FIG. 6.

FIG. 6 is a diagram representing the structure of the optical system of the reflection characteristic measuring apparatus 20*c* equipped with an illumination apparatus 10*c* as a fourth embodiment of the present invention. This reflection characteristic measuring apparatus 20*c* is similar to the aforementioned reflection characteristic measuring apparatuses 20, 20*a*, 20*b* and 20*b* except that only the illumination apparatus 10*c* is different from the aforementioned illumination apparatus 10, 10*a* and 10*b*. Accordingly, the corresponding portions will be assigned with the same reference symbols, and will not be described to avoid duplication. It should be noted that, when the second plane light source 12 is installed in this reflection characteristic measuring apparatus 20*c*, the second plane light source 12 is arranged at the position (on the farther side) opposite to the sample surface 1 with respect to the first plane light source 2 on the same normal 1*n*. In response thereto, as shown in FIG. 7, the polyhedral mirror 23 is provided with the first reflective surface 23*a* wherein the distance L11 from the normal 1*n* is equal to half the distance H1 between the sample surface 1 and the first plane light source 2, and the second reflective surface 23*b* wherein the distance L11 from the normal 1*n* is equal to half the distance H2 between the sample surface 1 and the second plane light source 12. In other words, the first reflective surface 23*a* in a section perpendicular to the normal forms a side of a polygon circumscribing an imaginary circle centered on the normal 1*n* and the radius is equal to half the distance H1 between sample surface 1 and the first plane light source 2. The second reflective surface 23*b* in a section perpendicular to the normal forms a side of a polygon circumscribing an imaginary circle centered on the normal and the radius is equal to half the distance H2 between the sample surface 1 and the second plane light source 12. The mask 24 located between the plane light sources 2 and 12 and the polyhedral mirror 23 is provided to restrict the emitted light fluxes 2*a* and 12*a*, in such a way that the light flux 2*a* emitted from the first plane light source 2 of a white LED will be reflected only by the first reflective surface 23*a* and the light flux 12*a* emitted from the second plane light source 12 of a violet LED will be reflected only by the second reflective surface 23*b* alone.

This structure ensures that the light flux 12*a* coming from the second plane light source 12 as the secondary light source and the light flux 2*a* coming from the first plane light source 2 as the main light source are reflected by the polyhedral mirror 23, and are converged on the sample surface 1 from multiple directions at an angle of incidence of 45 degrees with respect to the normal 1n. Thus, similarly to the case of the main light source, the secondary light source also increases the efficiency of the light flux usage while reducing the change in illuminance on the sample surface 1 caused by the fluctuation in the distance between the illumination apparatus and the sample surface. Further, this arrangement provides the advantage of the 45-degree c: 0-degree geometry which ensures greater stability against the inclination or anisotropy of the sample surface.

In the present embodiment, when the first plane light source is installed as the main light source and the second light source is further installed as the secondary light source for supplementing the spectral intensity distribution wherein the main light source does not have intensity, the second plane light source is arranged at the position (on the farther side) opposite to the sample surface with respect to the first plane light source. In response thereto, the polyhedral mirror incorporates the first reflective surface whose section perpendicular to the normal forms a side of a polygon circumscribing an imaginary circle centered on the normal and the radius is equal to half the distance H1 between the sample surface 1 and the first plane light source 2, and the second reflective surface whose section perpendicular to the normal forms a side of a polygon circumscribing an imaginary circle wherein the radius is equal to half the distance H2 between the sample surface 1 and the second plane light source 12. A plurality of the first reflective faces and the second reflective faces can alternately constitute the interior of the polyhedral mirror. Further, the first reflective face and the second reflective face may each circumscribe the imaginary circle or may be located intermediate between circumscribed and inscribed position.

Embodiment 5)

Figure 8:
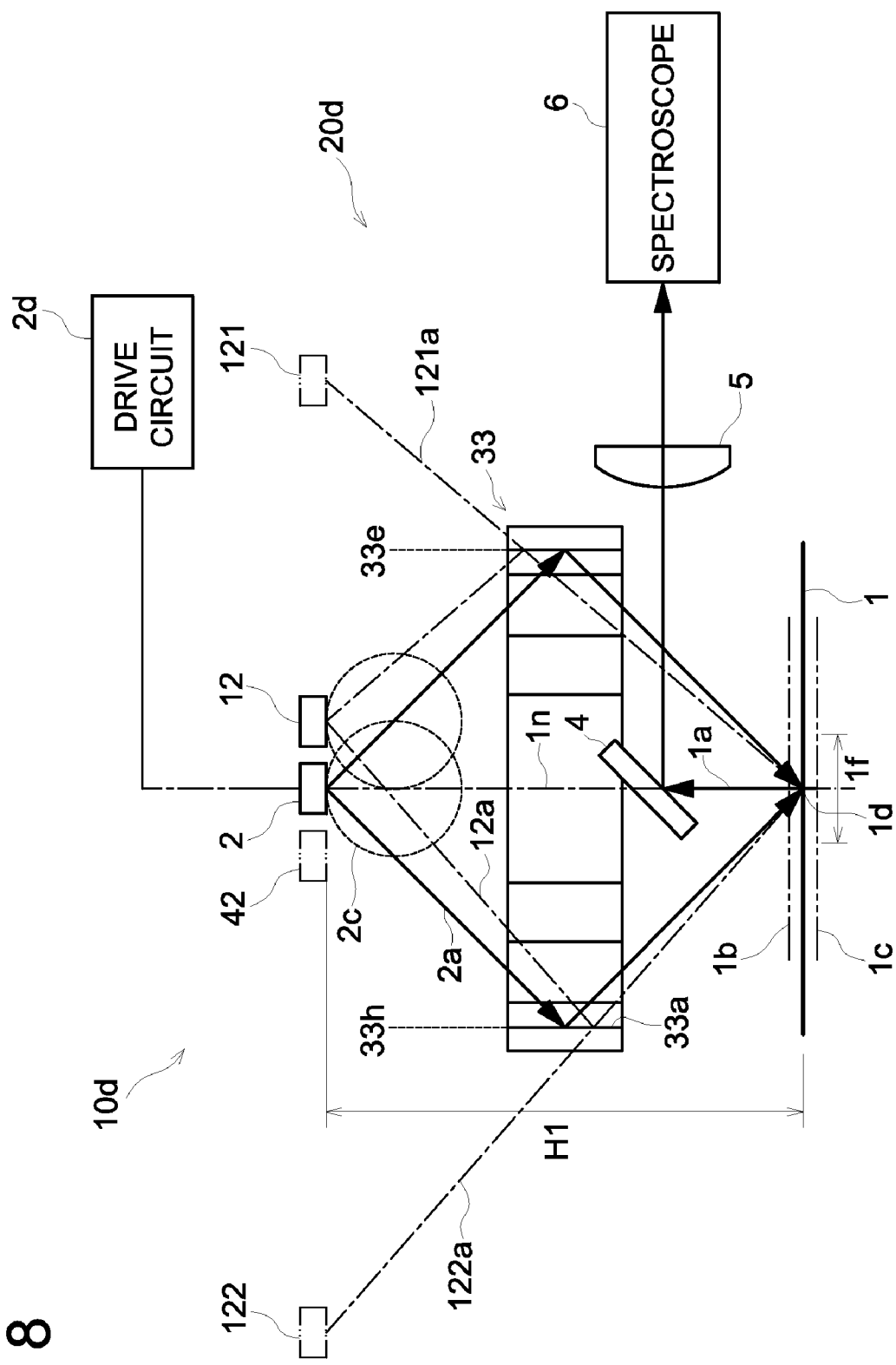
FIG. 8 is a diagram representing the structure of the optical system of the reflection characteristic measuring apparatus equipped with an illumination apparatus, as a fifth embodiment of the present invention.

FIG. 8 is a diagram representing the structure of the optical system of the reflection characteristic measuring apparatus 20d equipped with an illumination apparatus 10d as a fifth embodiment of the present invention. This reflection characteristic measuring apparatus 20d is similar to the aforementioned reflection characteristic measuring apparatuses 20, 20a, 20b and 20c except that only the illumination apparatus 10d is different from the illumination apparatuses 10, 10a, 10b and 20c. Accordingly, the corresponding portions will be assigned with the same reference symbols, and will not be described to avoid duplication. It should be noted that, when the second plane light source 12 is installed in this reflection characteristic measuring apparatus 20d, the second plane light source 12 is arranged in such a way that the distance (height H1) between the second plane light source 12 and sample surface 1 will be the same as the distance (height) between the first plane light source 2 and the surface including the sample surface 1, and the second plane light source 12 will be offset (in the lateral direction of the paper in FIG. 8) with respect to the normal 1n passing through the center 1d of the measured area 1f of the sample surface 1.

Figure 9:
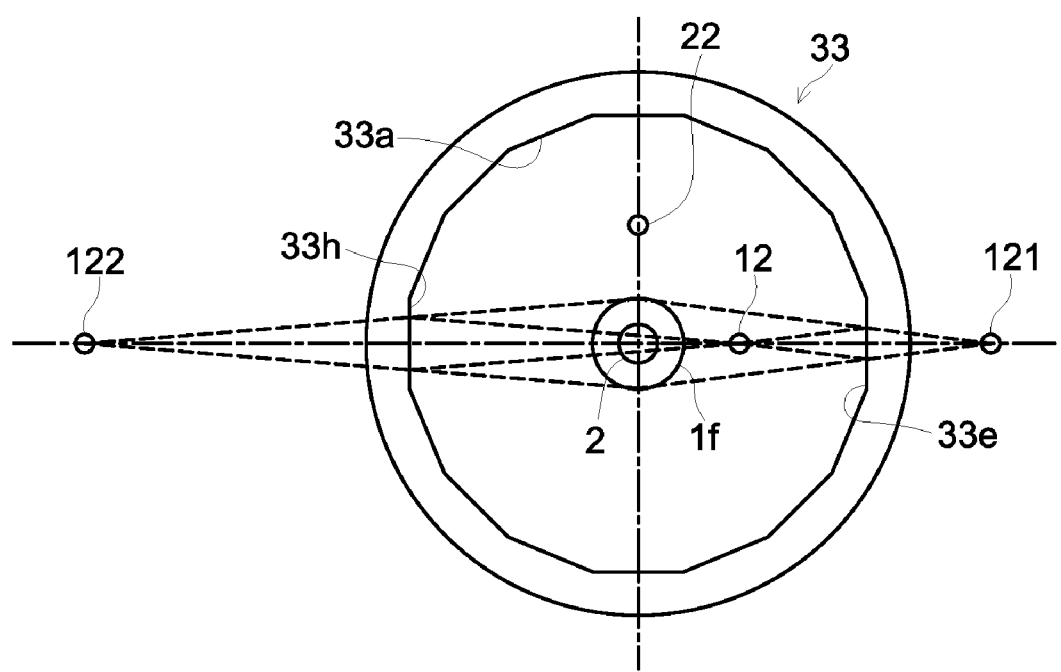
FIG. 9 is a plan view of FIG. 8.

In this case, out of the light flux emitted from the second plane light source 12 of the violet LED, a component reflected by the reflective faces 33e and 33h, opposed to each other, of the polyhedral mirror 33 reaches the measured area 1f of the sample surface 1, with the residual light flux hardly reaching it. To be more specific, as shown in FIG. 9 as a plan view of FIG. 8, the measured area 1f of the sample surface 1 is equivalently illuminated by the light flux emitted from the light source images (virtual source) 121 and 122 formed by the reflective face 33e and reflective face 33h which reflect light flux from the second plane light source 12. As described above, to reduce change ratio of the illuminance caused by the fluctuation in the distance, the reflective face 33e and reflective face 33h have a width perpendicular to the normal sufficient to reflect all the components of light flux which should reach the measured area of 1f sample surface.

Figure 10:
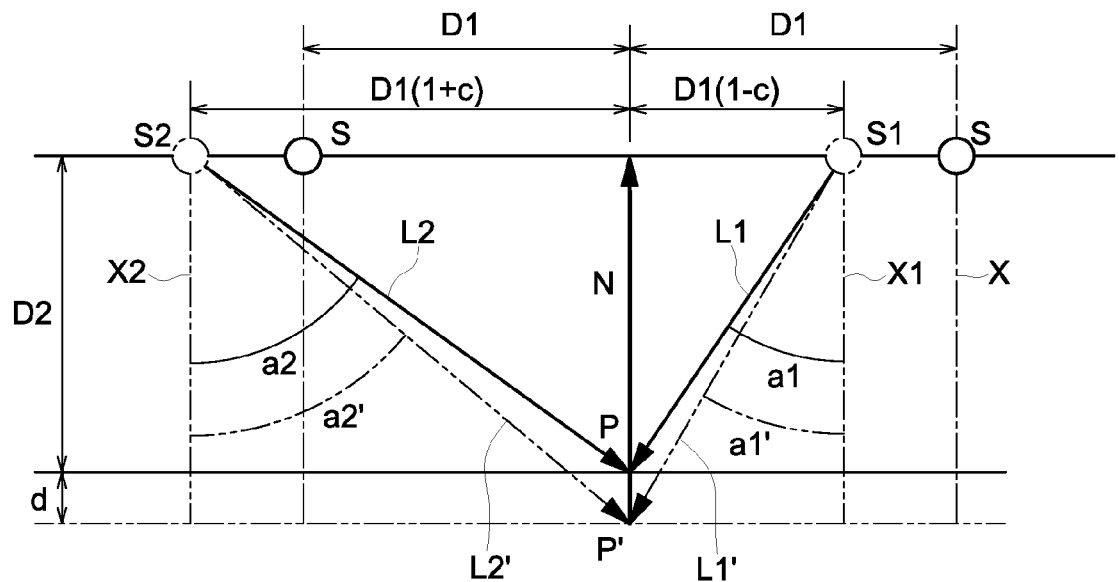
FIG. 10 is a conceptual diagram of an illumination optical system wherein the Lambertian light source is not located on the central axis of the measured area of a sample surface.

FIG. 10 is a conceptual diagram schematically representing the structure of FIG. 8. Assume that D2 denotes the distance between the sample surface 1 and the plane light sources 2 and 12, D1 indicates the distance between the normal N (1n in FIG. 8) of the polyhedral mirror 33 and the plane light source, and c·D1 represents the deviation from the normal N of the second plane light source 12. Then the light source images 121 and 122 formed by the reflective faces 33e and 33h, respectively, of FIG. 8 is expressed as two light sources S1 and S2 located at the distance D2 from the surface including the sample surface 1 and at the distance D1 (1−c) and D1(1+c), respectively, from the normal N. The image of the first plane light source 2 on the normal 1n is expressed by two light sources S wherein the distance from the normal N is D1. When considering the illumination by the second plane light source 12, the center P of the sample surface is illuminated by the light beams L1 and L2 in the spatial distribution of the light sources S1 and S2 having the Lambertian characteristics, wherein the light beams L1 and L2 have angles of incidence of a1 and a2, respectively, with respect to the center axes X1 and X2. When D1=D2, the angle a1 is smaller than 45 degrees and a2 is greater than 45 degrees.

The illumination at the center P of the sample surface by the light beams L1 and L2 coming from the light sources S1 and S2, respectively, is proportional to $\sin^2 (2 \cdot a1)$ and $\sin^2 (2 \cdot a2)$, respectively. When D1 (1−c) and D1 (1+c), which is the distance between the normal N and the light sources S1 and S2, respectively, is taken into account, the illuminance by two light beams L1 and L2 is proportional to $\sin^2 (2 \cdot a1)/(1-c)^2 + \sin^2 (2 \cdot a2)/(1+c)^2$. Differential coefficients of $\sin^2 (2 \cdot a1)$ and $\sin^2 (2 \cdot a2)$ are 0 at a1=45 degrees and a2=45 degrees, respectively. With the distance D1 (1−c) and D1 (1+c) of the light sources S1 and S2 from normal N, the differential coefficients are 0 at the positions displaced from distance D2=D1 by d=−c·D1 and d=c·D1, respectively. Thus, there are non-zero differential coefficients at the distance D2. The displacements −c·D1 and c·D1 are symmetric with each other, with respect to the distance D2 in-between, and therefore, two coefficients have almost the same magnitude with different signs, as far as c is not very large. Therefore, the influences upon the illuminances of the measured area 1f by the light sources S1 and S2 are considerably cancelled each other out and the influences to the total illuminance proportional to the $\sin^2 (2 \cdot a1)/(1-c)^2 + \sin^2 (2 \cdot a2)/(1+c)^2$ when the distance D2 has changed to D2+d is reduced considerably.

Figure 11:
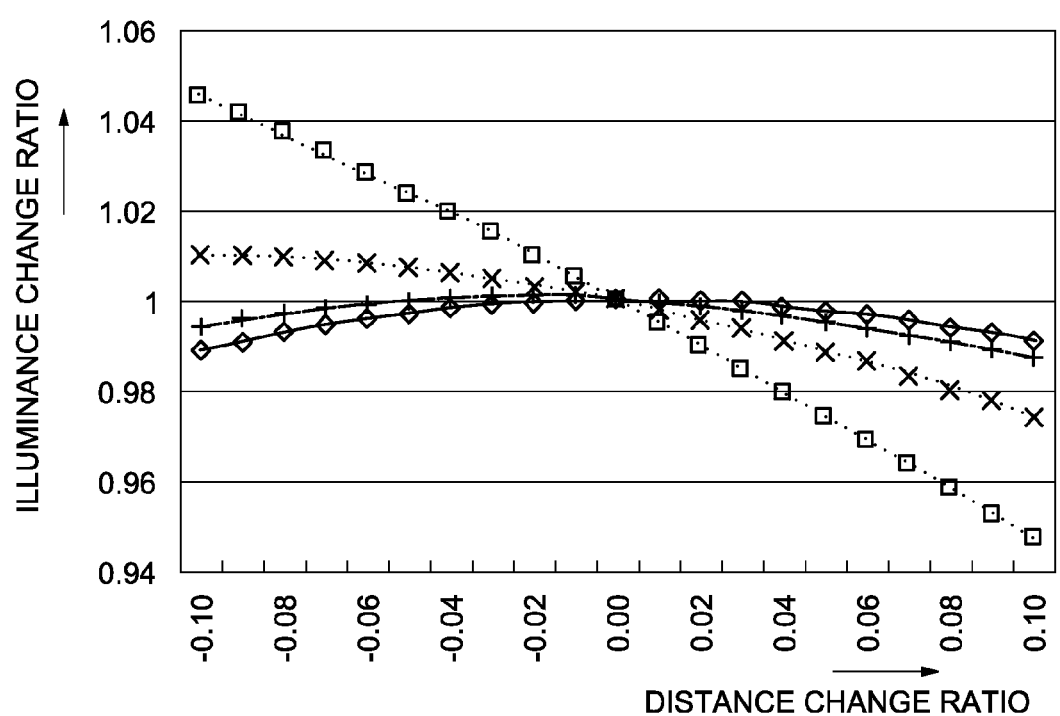
FIG. 11 is a chart showing changes in illuminance caused by fluctuations in the distance in the illumination optical system of FIG. 10.
Figure 15:
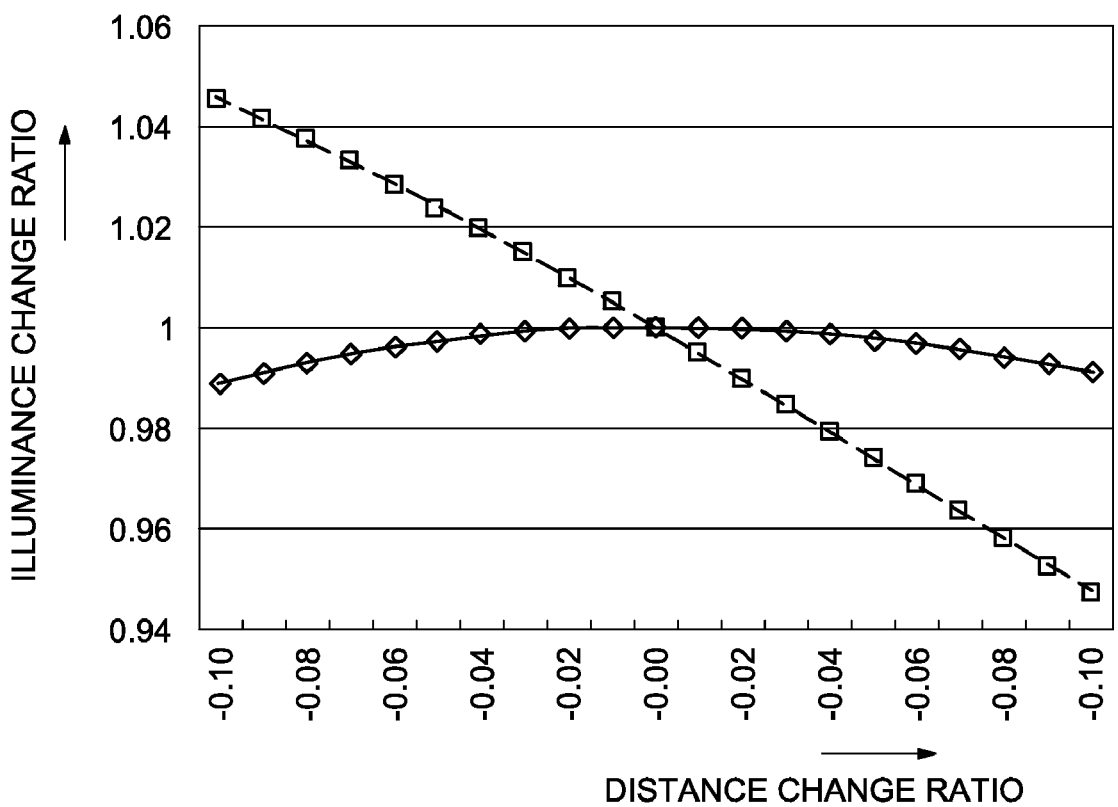
FIG. 15 is a chart showing changes in illuminance caused by the fluctuation in the distance between a light source and a sample surface in the illumination optical system of FIG. 14.

Similarly to the case of the aforementioned FIG. 15, FIG. 11 represents the performance of geometry of FIG. 10 for two cases—the light source with the spatial distribution of Lambertian characteristics (◇), and the light source with the uniform spatial distribution in the vicinity of 45 degrees independently of angle "a" (□). FIG. 11 shows changes in illuminance caused by the fluctuation d in the distance D2 between the light source at the offset c·D1 position from the normal N and the surface including the sample surface 1, for c=0.1 and 0.2, respectively. As will be apparent from the diagram, even if arrangement is offset by 20% of the distance D1 (represented by x), a change in illuminance caused by the fluctuation of 5% of the distance D2 does not exceed 0.5% with the light source of Lambertian characteristics. This is less than half the change in illuminance in the light source with non-Lambertian characteristics located on the normal N (□). If the offset is 10% (+), the change in illuminance is approximately one fourth.

This arrangement allows installment of the secondary light source supplementing the spectral intensity distribution uncovered by the first light source without any remarkable structural addition or change. In this arrangement, usage of the light flux from the secondary light source is restricted and the efficiency is low. However, as the wavelength range covered by the secondary light source is restricted to a narrow range and the sufficient intensity can be obtained. Since this arrangement forms a 45-degree b : 0-degree geometry (b: bidirectional) for the secondary light source wherein illumination is given by light fluxes in the vicinity of two directions facing with each other, influence of the inclination and anisotropy of the sample surface 1 can be partially reduced. To further reduce the influence of the inclination and anisotropy, the third plane light source 22 of the same violet LED should be arranged in the direction perpendicular to the second plane light source 12 of the violet LED, as shown in FIG. 9.

Supplementing the main light source positioned on the normal 1n, different types of light sources as the secondary light source may be installed at offset position. For example, as shown in FIG. 8, in addition to the first plane light source 2 of the white LED as the main light source, the second plane light source 12 of the violet LED as the first secondary light source and the fourth plane light source 42 of the ultraviolet LED as the second secondary light source can be arranged on both sides of the first plane light source 2. In this case, the overall visible spectrum can be covered by using the violet LED as the first secondary light source. Use of the ultraviolet LED as the second secondary light source makes it possible to measure the sample surface including the fluorescent whitening agent which emits visible light converted from the ultraviolet component of the illumination. Further, more secondary light sources may be arranged around the first plane light source 2 in conformity to the reflective faces 33a of the polyhedral mirror 33.

Figure 12:
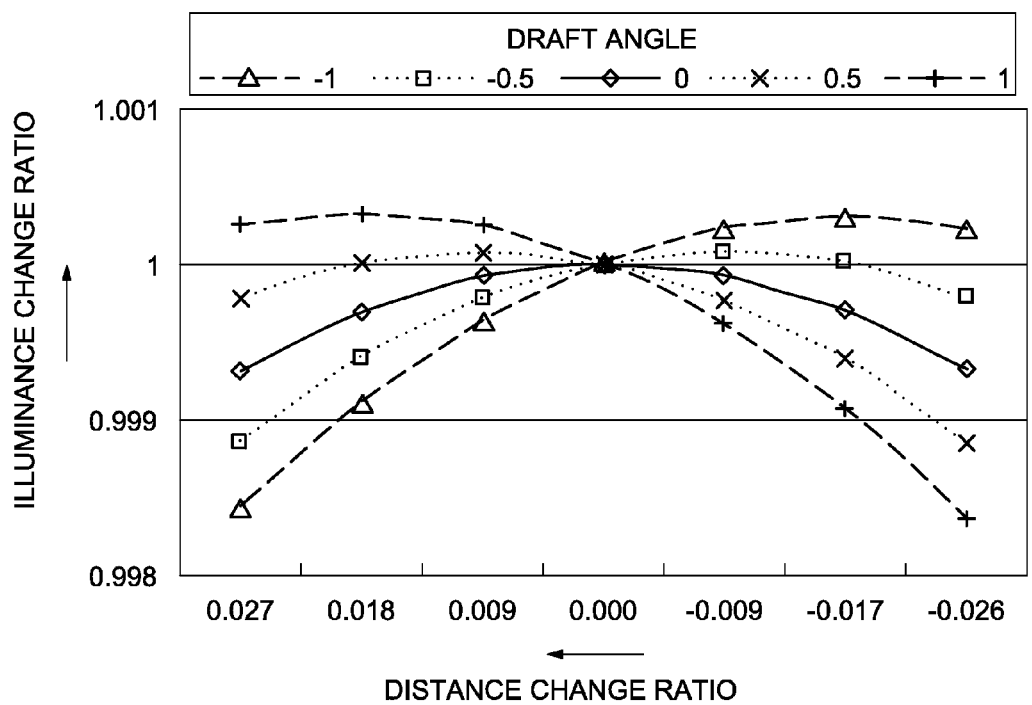
FIG. 12 is a chart showing changes in illuminance caused by fluctuations in the distance between a light source and a sample surface when the polyhedral mirror is molded with draft angle.

In the aforementioned embodiments, the polyhedral mirror needs not always be a continuous (connected throughout the entire surface) cylindrical member. The polyhedral mirror can be separated as appropriate in conformance to the support member of the component for the receiving optical system. Further, the polyhedral mirror 33 can be formed as polygonal slightly opened to one end. This makes it possible to provide a draft required for plastic injection molding, and permits easy production of a polyhedral mirror 33 at reduced costs. FIG. 12 shows the change in illuminance caused by the fluctuation in the distance when the draft is set at 0 degree, ±0.5 degree and ±1 degree (+ indicates a polygonal tube opened downward, and – denotes the polygonal tube opened upward). For example, consider the change in illuminance caused by the fluctuation in the distance corresponding to distance D2±3% (approximately). Even when the polyhedral mirror 3 is assumed as a polygonal tube opened downward opening at one degree (+), the change caused by the distant fluctuation of 3% in illuminance is about 0.2%, which is sufficiently small for a practical use.

Embodiment 6)

Figure 13:
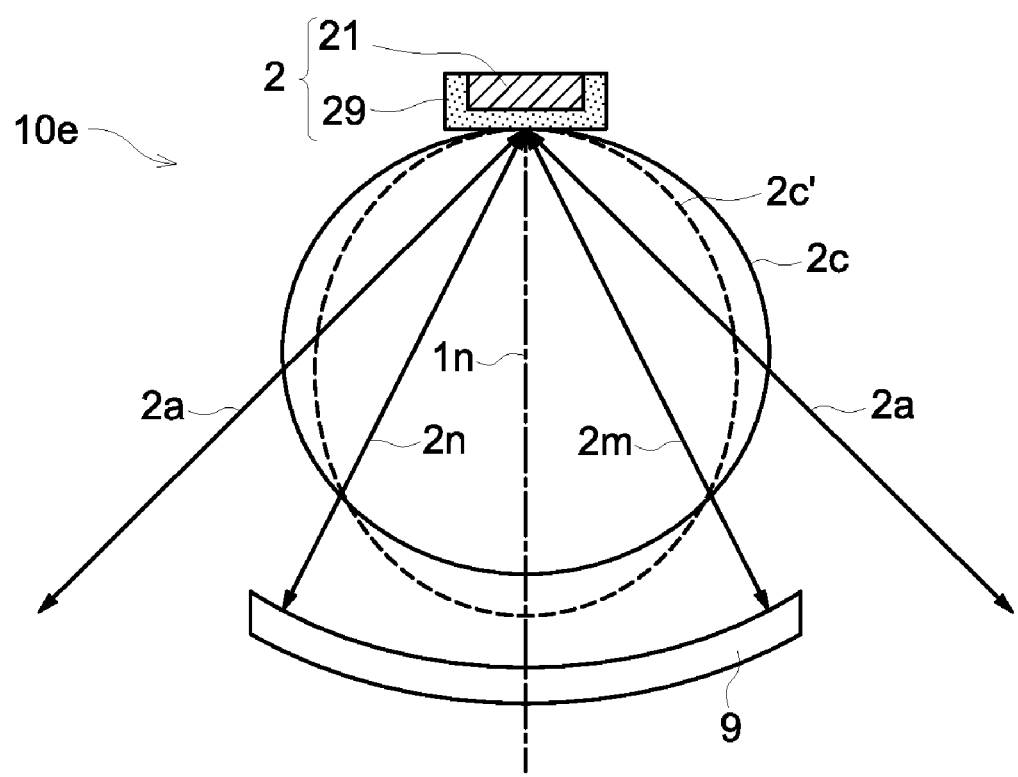
FIG. 13 is a diagram showing the structure of an optical system of an illumination apparatus, as a sixth embodiment of the present invention.
Figure 14:
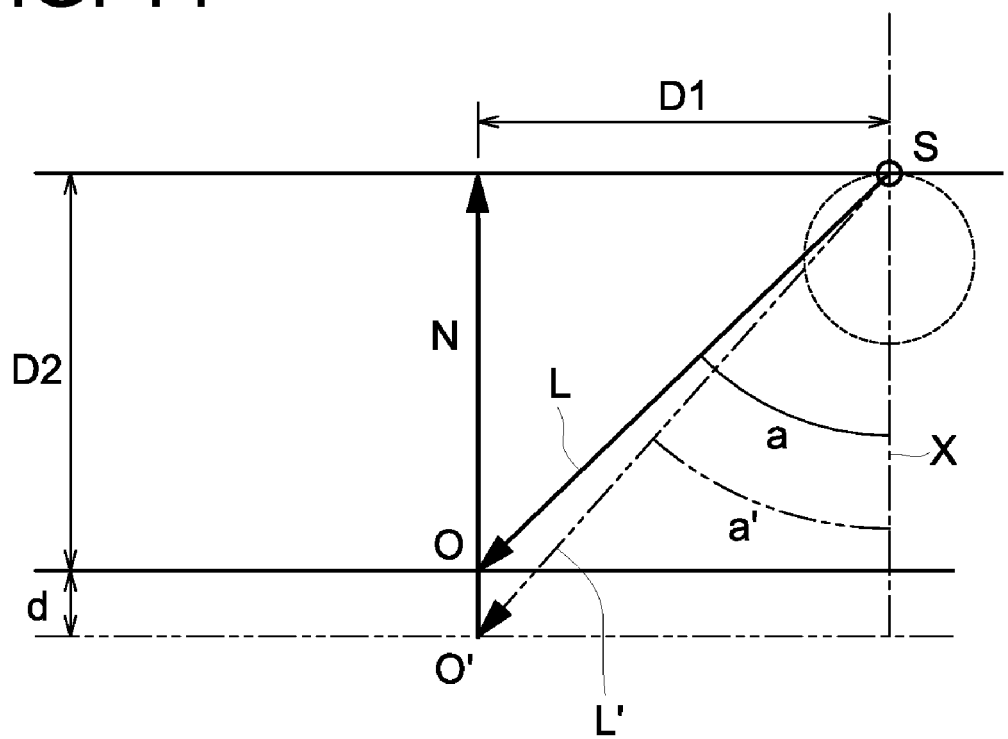
FIG. 14 is a conceptual diagram of an illumination optical system using a conventional light source of the Lambertian characteristics.

FIG. 13 is a diagram showing the structure of the optical system of the illumination apparatus 10e as a sixth embodiment of the present invention. This illumination apparatus 10e is applicable to each of the aforementioned reflection characteristic measuring apparatuses 20 and 20a and others. In this case, a white LED used as the first plane light source 2 and having the spectral distribution of FIG. 5 includes an LED chip 21 for emitting blue light in the vicinity of 450 nm, and a resin layer 29 containing the fluorescent powder coated on the LED chip 21, as shown in FIG. 13. To improve the scattering property, powdered titanium oxide is added to the resin layer 29 in some cases. This structure allows part of the blue light emitted from the LED chip 21 to be converted to the fluorescence having a wide band centering on 600 nm or thereabout by the fluorescent powder of the resin layer 29. The other part is scattered and radiated by fluorescent powder or powdered titanium oxide. Intrinsically, the fluorescence has spatial distribution of the substantially Lambertian characteristics indicated by the reference symbol 2c in FIG. 13, and the arrangement of FIG. 1 or others reduces the change in illuminance caused by the fluctuation in the distance between the illumination apparatus 10 and the sample surface 1.

In case of a blue light, when there is a small amount of fluorescent powder or powdered titanium oxide in it, the blue light is radiated more in the directions near the center axis of the Lambertian distribution, as indicated by the reference symbol 2c'. Therefore, in some cases, the change in illuminance caused by the fluctuation in the distance cannot be reduced sufficiently by the arrangement of FIG. 1 or others. To be more specific, the influence of the fluctuation in the distance differs according to the wavelength range, and this may cause an enhanced error in color value (tint) which raises a big problem.

To solve this problem, in this illumination apparatus 10e, the concave mirror 9 wherein the spherical center is located at the center of the white LED is arranged on the optical axis 1n to reflect the light flux component 2m back on to the white LED while light flux 2a reaches the polyhedral mirror 33 or the cylindrical surface mirror 3. Thus, the image of the white LED is formed on the white LED and is radiated again. The light flux reflected by the concave mirror 9 and inputted again to the white LED is scattered and reflected by the resin layer 29. Since a distance of the optical path inside the resin layer becomes longer when a light flux is reflected by the layer than transmitted through the layer, scattering caused by the fluorescent powder and powdered titanium oxide increases when the light flux is reflected by the layer. This brings the spatial distribution characteristics from the state of reference symbol 2c' closer to the Lambertian characteristics denoted by the reference symbol 2c, thereby improving the effect of reducing the change in illuminance caused by the fluctuation in the distance, as described above. Further, the light flux emitted in the vicinity of normal 1n which has higher intensity is reused, whereby the efficiency of the light flux usage is increased.

As described above, when illuminating the sample surface for measuring the spectral reflection characteristics, the illumination apparatus and the reflection characteristic measuring apparatus using the same in the present invention are designed in such a way that the light source arranged on the normal of the sample surface passing through the center of the measured area, as a plane light source of the LED, for example, is characterized by the spatial distribution of the Lambertian characteristics (cosine characteristic), and the light flux emitted by the plane light source is reflected by the cylindrical surface mirror having the internal reflective surface arranged between the sample surface and the plane light source, wherein the section of the reflective surface in a plane perpendicular to the normal is circular, and the radius of the imaginary circle is substantially equal to half the distance between the sample surface and the plane light source, whereby the sample surface is illuminated.

This arrangement ensures that the sample surface is illuminated from the direction of 45 degrees with respect to the normal, and the light reflected by the sample surface is received from the direction of the normal, whereby the so-called 45-degree: 0-degree geometry is implemented. Further, the sample surface is equivalently illuminated by the numberless light source images of Lambertian characteristics on the circumference whose radius is equal to the distance between the sample surface and the plane light source, wherein the plane light source is at the center. Thus, the change in illuminance caused by the fluctuation in the distance between the light source and the sample surface can be reduced. At the same time, the light flux emitted from the plane light source in all azimuthal directions in the vicinity of 45 degrees with respect to the center axis of the spatial distribution can be converged on the sample surface, whereby the efficiency of using the light flux can be improved. Illumination from all azimuthal directions provides the advantage of the 45-degree a: 0-degree geometry which ensures greater stability against the inclination or anisotropy of the sample surface.

As described above, when illuminating the sample surface for measuring the spectral reflection characteristics, the illumination apparatus and the reflection characteristic measuring apparatus using the same in the present invention are designed in such a way that the light source arranged on the normal of the sample surface passing through the center of the measured area, as a plane light source of the LED and others, has the spatial distribution of the Lambertian characteristics (cosine characteristic), and the light flux emitted by the plane light source is reflected by the polyhedral reflective faces arranged between the sample surface and the plane light source, wherein the section in a plane perpendicular to the normal is polygonal, and this polygon circumscribes an imaginary circle whose radius is half the distance between the sample surface and the plane light source, whereby the sample surface is illuminated.

This arrangement ensures the sample surface to be illuminated from the direction of 45 degrees with respect to the normal, and light reflected by the sample surface is received from the direction of the normal, whereby the so-called 45-degree: 0-degree geometry is implemented. Further, the sample surface is equivalently illuminated by a pluarity of light source images of Lambertian characteristics on the circumference whose radius is equal to the distance between the sample surface and the plane light source, wherein the plane light source is used as a center. Thus, the change in illuminance caused by the fluctuation in the distance between the light source and the sample surface can be reduced. At the same time, the majority of the light flux emitted in all azimuthal directions from the plane light source can be converged on the sample surface, whereby the efficiency of the light flux usage can be improved. Illumination from multiple directions by a plurality of reflective faces provides the advantage of the 45-degree c: 0-degree geometry which ensures greater stability against the inclination or anisotropy of the sample surface.

Although the invention has been described with reference to the preferred embodiments, it will be apparent to one skilled in the art that variations and modifications are contemplated within the spirit and scope of the invention. The drawings and description of the preferred embodiments are made by way of example rather than to limit the scope of the invention, and it is intended to cover within the spirit and scope of the invention all such changes and modifications.

What is claimed is:

1. An illumination apparatus for illuminating a sample surface to be measured, the illumination apparatus comprising:

a plane light source having a spatial distribution of Lambertian characteristic positioned on a normal passing through a center of a measured area of the sample surface; and a mirror having an internal reflective surface being positioned between said plane light source and said measured area of the sample surface so as to reflect light from the plane light source to the measured area so that the light reflected on said internal reflective surface directly enters the measured area keeping the spatial distribution of Lambertian characteristic at an angle of 45 degrees with respect to the normal, said internal reflective surface having a circular or polygonal shape in a section perpendicular to said normal, said circular or polygonal shape substantially corresponding to an imaginary circle which is centered on said normal and has a radius equal to half a distance between said plane light source and said measured area of the sample surface.

2. An illumination apparatus of claim 1, wherein said polygonal shape circumscribes said imaginary circle.

3. An illumination apparatus of claim 1, wherein said internal reflective surface have a discontinuous circular or polygonal shape in a section perpendicular to said normal.

4. An illumination apparatus of claim 1, wherein said plane light source comprises an LED.

5. An illumination apparatus of claim 1, further comprising a secondary light source having spectral intensity distribution supplemental to spectral intensity distribution of said plane light source.

6. An illumination apparatus of claim 5, wherein said secondary light source is a second plane light source.

7. An illumination apparatus of claim 6, where said plane light source is called as a first plane light source and said secondary light source is called as a second plane light source, further comprising a combining member which is adapted to combine the light from the first plane light source and the light from the second plane light source.

8. An illumination apparatus of claim 1, further comprising a concave mirror positioned between said plane light source and said measured area of the sample surface to reflect light from the plane light source back to the measured area.

9. An illumination apparatus for illuminating a sample surface to be measured, the illumination apparatus comprising:

a plane light source positioned on a normal passing through a center of a measured area of the sample surface; and a mirror having an internal reflective surface being positioned between said plane light source and said measured area of the sample surface for reflecting light from the plane light source to the measured area, said internal reflective surface having a circular or polygonal shape in a section perpendicular to said normal, said circular or polygonal shape substantially corresponding to an imaginary circle which is centered on said normal and has a radius equal to half a distance between said plane light source and said measured area of the sample surface;

a secondary light source having spectral intensity distribution supplemental to spectral intensity distribution of said plane light source, said secondary light source is a second plane light source; and a combining member which is adapted to combine the light from the first plane light source and the light from the second plane light source;

wherein said combining member comprises a dichroic mirror or a semi-transmissive mirror positioned between said first plane light source and said internal reflective surface.

10. An illumination apparatus of claim 9, where said second plane light source is positioned symmetrically to said first plane light source with respect to said combining member.

11. An illumination apparatus for illuminating a sample surface to be measured, the illumination apparatus comprising:
a plane light source positioned on a normal passing through a center of a measured area of the sample surface; and
a mirror having an internal reflective surface being positioned between said plane light source and said measured area of the sample surface for reflecting light from the plane light source to the measured area, said internal reflective surface having a circular or polygonal shape in a section perpendicular to said normal, said circular or polygonal shape substantially corresponding to an imaginary circle which is centered on said normal and has a radius equal to half a distance between said plane light source and said measured area of the sample surface;
a secondary light source having spectral intensity distribution supplemental to spectral intensity distribution of said plane light source, said secondary light source is a second plane light source; and
wherein said second plane light source is positioned on an opposite side to said measured area of the sample surface with respect to the first plane light source.

12. An illumination apparatus of claim 11, wherein said internal reflective surface has another circular or polygonal shape in a section perpendicular to said normal, said circular or polygonal shape substantially corresponding to another imaginary circle which is centered on said normal and has a diameter equal to a distance between said second plane light source and said measured area of the sample surface.

13. An illumination apparatus for illuminating a sample surface to be measured, the illumination apparatus comprising:
a plane light source positioned on a normal passing through a center of a measured area of the sample surface; and
a mirror having an internal reflective surface being positioned between said plane light source and said measured area of the sample surface for reflecting light from the plane light source to the measured area, said internal reflective surface having a circular or polygonal shape in a section perpendicular to said normal, said circular or polygonal shape substantially corresponding to an imaginary circle which is centered on said normal and has a radius equal to half a distance between said plane light source and said measured area of the sample surface;
a secondary light source having spectral intensity distribution supplemental to spectral intensity distribution of said plane light source, said secondary light source is a second plane light source; and
wherein a distance between said second plane light source and said measured area of the sample surface is equal to a distance between said first plane light source and the measured area of the sample surface, and wherein the second plane light source is placed off said normal.

14. An illumination apparatus for illuminating a sample surface to be measured, the illumination apparatus comprising:
a plane light source having a spatial distribution of Lambertian characteristic positioned on a normal passing through a center of a measured area of the sample surface; and
a plurality of reflective faces being positioned between said plane light source and said measured area of the sample surface and in parallel to said normal so as to reflect light from the plane light source to the measured area so that the light reflected on the reflective faces directly enters the measured area keeping the spatial distribution of Lambertian characteristic at an angle of 45 degrees with respect to the normal, said reflective surfaces being positioned at a distance from said normal half as long as a distance between the plane light source and the measure area.

15. An illumination apparatus of claim 14, wherein said plane light source comprises an LED.

16. An illumination apparatus of claim 14, further comprising a secondary light source having spectral intensity distribution supplemental to spectral intensity distribution of said plane light source.

17. An illumination apparatus of claim 16, wherein said secondary light source is a second plane light source.

18. An illumination apparatus of claim 17, where said plane light source is called as a first plane light source and said secondary light source is called as a second plane light source further comprising a combining member which is adapted to combine the light from the first plane light source and the light from the second plane light source.

19. An illumination apparatus for illuminating a sample surface to be measured, the illumination apparatus comprising:
a plane light source positioned on a normal passing through a center of a measured area of the sample surface; and
a plurality of reflective faces being positioned between said plane light source and said measured area of the sample surface and in parallel to said normal for reflecting light from the plane light source to the measured area, said reflective surfaces being positioned at a distance from said normal half as long as a distance between the plane light source and the measure area;
a secondary light source having spectral intensity distribution supplemental to spectral intensity distribution of said plane light source, said secondary light source is a second plane light source; and
a combining member which is adapted to combine the light from the first plane light source and the light from the second plane light source;
wherein said combining member comprises a dichroic mirror or a semi-transmissive mirror positioned between said first plane light source and said reflective faces.

20. An illumination apparatus of claim 19, where said second plane light source is positioned symmetrically to said first plane light source with respect to said combining member.

21. An illumination apparatus for illuminating a sample surface to be measured, the illumination apparatus comprising:
a plane light source positioned on a normal passing through a center of a measured area of the sample surface; and
a plurality of reflective faces being positioned between said plane light source and said measured area of the sample surface and in parallel to said normal for reflecting light from the plane light source to the measured area, said reflective surfaces being positioned at a distance from said normal half as long as a distance between the plane light source and the measure area;

a secondary light source having spectral intensity distribution supplemental to spectral intensity distribution of said plane light source, said secondary light source is a second plane light source; and wherein said second plane light source is positioned on an opposite side to said measured area of the sample surface with respect to the first plane light source.

22. An illumination apparatus of claim 21, wherein other reflective faces are positioned at a distance from said normal equal to half a distance between said second plane light source and the measured area of the sample surface.

23. An illumination apparatus for illuminating a sample surface to be measured, the illumination apparatus comprising:
  a plane light source positioned on a normal passing through a center of a measured area of the sample surface; and
  a plurality of reflective faces being positioned between said plane light source and said measured area of the sample surface and in parallel to said normal for reflecting light from the plane light source to the measured area, said reflective surfaces being positioned at a distance from said normal half as long as a distance between the plane light source and the measure area;
  a secondary light source having spectral intensity distribution supplemental to spectral intensity distribution of said plane light source, said secondary light source is a second plane light source; and
  wherein a distance between said second plane light source and said measured area of the sample surface is equal to a distance between said first plane light source and the measured area of the sample surface, and wherein the second plane light source is placed off said normal.

24. A reflection characteristics measuring apparatus comprising:
  a plane light source having a spatial distribution of Lambertian characteristic positioned on a normal passing through a center of a measured area of the sample surface;
  a mirror having an internal reflective surface being positioned between said plane light source and said measured area of the sample surface so as to reflect light from the plane light source to the measured area so that the light reflected on said internal reflective surface directly enters the measured area keeping the spatial distribution of Lambertian characteristic at an angle of 45 degrees with respect to the normal, said internal reflective surface having a circular or polygonal shape in a section perpendicular to said normal, said circular or polygonal shape substantially corresponding to an imaginary circle which is centered on said normal and has a diameter equal to a distance between said plane light source and said measured area of the sample surface; and
  a measuring section, which is adapted to measure reflective characteristic of said measured area of the sample surface based on a light reflected by the measured area of the sample surface.

25. A reflective characteristics measuring apparatus of claim 24, wherein said measuring section comprises a reflective mirror which is positioned on said normal to reflect a light from said measured area to the direction parallel to said measured area of the sample surface.

26. A reflective characteristics measuring apparatus of claim 24, wherein said measuring section comprises an optical lens adapted to converge light reflected by said measured area of the sample surface.

27. A reflective characteristic measuring apparatus of claim 24, wherein said measuring section comprises a spectrometer adapted to convert spectral components of light reflected by said measured area of the sample into corresponding electrical signals.

28. A reflection characteristics measuring apparatus comprising:
  a plane light source having a spatial distribution of Lambertian characteristic positioned on a normal passing through a center of a measured area of the sample surface;
  a plurality of reflective faces being positioned between said plane light source and said measured area of the sample surface and in parallel to said normal so as to reflect light from the plane light source to the measured area so that the light reflected on the reflective faces directly enters the measured area keeping the spatial distribution of Lambertian characteristic at an angle of 45 degrees with respect to the normal, said reflective surfaces being positioned at a distance from said normal half as long as a distance between the plane light source and the measure area; and
  a measuring section, which is adapted to measure reflective characteristics of said measured area of the sample surface based on a light reflected by the measured area of the sample surface.

29. A reflective characteristics measuring apparatus of claim 28, wherein said measuring section comprises a reflective mirror which is positioned on said normal to reflect a light from said measured area to the direction parallel to said measured area of the sample surface.

30. A reflective characteristics measuring apparatus of claim 28, wherein said measuring section comprises an optical lens adapted to converge light reflected by said measured area of the sample surface.

31. A reflective characteristics measuring apparatus of claim 28, wherein said measuring section comprises a spectrometer adapted to convert spectral components of light reflected by said measured area of the sample into corresponding electrical signals.

* * * * *